United States Patent
Schwaab et al.

(10) Patent No.: US 11,254,914 B2
(45) Date of Patent: Feb. 22, 2022

(54) ENRICHMENT OF CD16+ MONOCYTES TO IMPROVE DENDRITIC CELL VACCINE QUALITY

(71) Applicant: HEALTH RESEARCH, INC., Buffalo, NY (US)

(72) Inventors: Thomas Schwaab, Amherst, NY (US); Jason Bryan Muhitch, Amherst, NY (US)

(73) Assignee: HEALTH RESEARCH, INC., Buffalo, NY (US)

( * ) Notice: Subject to any disclaimer, the term of this patent is extended or adjusted under 35 U.S.C. 154(b) by 91 days.

(21) Appl. No.: 15/557,290

(22) PCT Filed: Mar. 11, 2016

(86) PCT No.: PCT/US2016/022018
§ 371 (c)(1),
(2) Date: Sep. 11, 2017

(87) PCT Pub. No.: WO2016/145317
PCT Pub. Date: Sep. 15, 2016

(65) Prior Publication Data
US 2018/0127716 A1    May 10, 2018

Related U.S. Application Data

(60) Provisional application No. 62/132,192, filed on Mar. 12, 2015, provisional application No. 62/132,206, filed on Mar. 12, 2015.

(51) Int. Cl.
*A61K 35/15* (2015.01)
*C12N 5/0784* (2010.01)

(52) U.S. Cl.
CPC ............ *C12N 5/0639* (2013.01); *A61K 35/15* (2013.01); *C12N 2501/02* (2013.01);
(Continued)

(58) Field of Classification Search
CPC .............. C12N 5/0639; C12N 2501/15; C12N 2501/23; C12N 2501/02; C12N 2501/22;
(Continued)

(56) References Cited

U.S. PATENT DOCUMENTS

2006/0002899 A1    1/2006    Rice et al.
2006/0078994 A1    4/2006    Healey et al.

FOREIGN PATENT DOCUMENTS

WO    2001027245    4/2001
WO    WO-2013127976 A1 *  9/2013    ............. A61K 39/12
(Continued)

OTHER PUBLICATIONS

Randolph et al. "The CD16+ subset of human monocytes preferentially becomes migratory dendritic cells in a model tissue setting" J Exp Med, Aug. 19, 2002; 196(4):517-27. (Year: 2002).*
(Continued)

*Primary Examiner* — Blaine Lankford
*Assistant Examiner* — Lauren K Van Buren
(74) *Attorney, Agent, or Firm* — Nixon Peabody LLP; Mark J. FitzGerald

(57) ABSTRACT

Compositions and methods are provided for converting the predominant circulating classical monocytes to a non-classical and/or intermediate monocyte phenotype through cytokine stimulation via, for example, macrophage colony-stimulating factor. Once cultured into dendritic cells, these non-classical and/or intermediate monocyte derived cells have increased costimulatory molecule expression, which leads to improved immune and clinical responses in cancer patients receiving dendritic cell vaccination and other immunotherapies. In addition, assays and diagnostic and therapostic methods are provided herein that relate to the discoveries that, prior to treatment, intermediate (CD14+CD16+) and non-classical (CD14dimCD16+) monocytes are
(Continued)

increased more than two-fold in patients who later had complete responses to dendritic cell therapy or DC vaccination.

8 Claims, 7 Drawing Sheets

Specification includes a Sequence Listing.

(52) U.S. Cl.
CPC ...... *C12N 2501/15* (2013.01); *C12N 2501/22* (2013.01); *C12N 2501/23* (2013.01); *C12N 2501/2304* (2013.01); *C12N 2501/2306* (2013.01); *C12N 2501/25* (2013.01); *C12N 2501/998* (2013.01); *C12N 2506/115* (2013.01)

(58) Field of Classification Search
CPC .... C12N 2501/2304; C12N 2501/2306; C12N 2501/25; C12N 2501/998; C12N 2506/115; A61K 35/15
See application file for complete search history.

(56) References Cited

FOREIGN PATENT DOCUMENTS

| WO | 2014127917 | 8/2014 |
|----|------------|--------|
| WO | 2014168874 | 10/2014 |
| WO | 2015069770 | 5/2015 |

OTHER PUBLICATIONS

West et al. "Transforming Growth Factor-beta, Macrophage Colony Stimulating Factor, and C-reactive protein Levels Correlates with CD14 CD16 Monocyte Induction and Activation in Trauma Patients" Dec. 2012 vol. 7, Issue 12. (Year: 2012).*

Sanchez-Torres "CD16 and CD16− human blood monocyte subsets differentiate in vitro to dendritic cells with different abilities to stimulate CD4 T cells" International Immunology, vol. 13. No. 12, pp. 1571-1581 (Year: 2001).*

Randolph et al. The CD16+ subsets of human monocytes preferentially becomes migratory dendritic cells in a model tissue setting J. Exp. Med., Aug. 19, 2002; 196(4): 517-27 (Year: 2002).*

Omata et al. "Monocyte Chemoattractant Protein-1 Selectively Inhibits the Acquisition of CD40 Ligand-Dependent IL-12 Producing Capacity of Monocyte-Derived Dendritic Cells and Modulates Th1 Immune Reponse" J. Immunology 2002; 169, 4861-4866 (Year: 2002).*

Yang et al. "Monocyte and macrophage differentiation: circulation inflammatory monocyte as biomarker for inflammatory disease" Biomarker Reserach 2014, 2:1 (Published Jan. 2014) (Year: 2014).*

Randolph, et al., "the CD16(+)(FcgammaRIII(+)) subset of human monocytes preferentially becomes migratory dendritic cells in a model tissue setting," J Exp Med. Aug. 19, 2002, vol. 196, No. 4, pp. 517-527.

Lee et al., "Immunotherapy using autologous monocyte-derived dendritic cells pulsed with leukemic cell lysates for acute myeloid leukemia relapse after autologous peripheral blood stem cell transplantation." Journal of Clinical Apheresis: The Official Journal of the American Society for Apheresis 19(2):66-70 (2004).

Li et al. "TGF-β combined with M-CSF and IL-4 induces generation of immune inhibitory cord blood dendritic cells capable of enhancing cytokine-induced ex vivo expansion of myeloid progenitors." Blood 110(8):2872-2879 (2007).

Li et al., "Interleukin-10 in combination with M-CSF and IL-4 contributes to development of the rare population of CD14+ CD16++ cells derived from human monocytes." Biochemical and Biophysical Research Communications 322(2):637-643 (2004).

Muhitch et al., "MP47-16 Pretreatment Peripheral Blood Monocyte Subset Signature in Stage IV Renal Cell Carcinoma Patients Predicts Outcome to Dendritic Cell Vaccination." The Journal of Urology 193(4):e557-e558 (2015).

* cited by examiner

ENRICHMENT OF CD16+ MONOCYTES TO IMPROVE DENDRITIC CELL VACCINE QUALITY

CROSS-REFERENCE TO RELATED APPLICATIONS

This application is a 35 U.S.C. § 371 National Phase Entry Application of International Application No. PCT/US2016/022018 filed Mar. 11, 2016, which designated the U.S., and which claims benefit under 35 U.S.C. § 119(e) of U.S. Provisional Application Ser. No. 62/132,192 filed Mar. 12, 2015 and U.S. Provisional Application Ser. No. 62/132,206 filed Mar. 12, 2015, the contents of each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Dec. 7, 2017, is named 042515-000029-US_SL.txt and is 644 bytes in size.

TECHNICAL FIELD

The technical field relates to compositions and methods for enhancing dendritic cell vaccine quality.

BACKGROUND

A critical barrier to successful cancer treatment is the inability to initiate durable, tumor-specific responses with conventional therapy such as chemotherapy or radiation. Compared to traditional therapies, immune-based strategies can generate long-lasting systemic protection. Immunotherapy has a potential role for all cancer types. Dendritic cell (DC) vaccination is an immunotherapy designed to induce cancer-specific T cell-dependent anti-tumor immunity that can result in durable, complete responses. Recent advances in protocols that utilize dendritic cells electroporated with autologous tumor RNA (AGS-003) have led to sustained immune responses with improved patient survival.

SUMMARY

The compositions and methods described herein are based, in part, on the discovery that DCs derived from intermediate and non-classical monocytes represent the most potent antigen presenting cells for use in dendritic cell vaccination. As demonstrated herein, DCs derived from non-intermediate and/or classical monocytes have improved costimulatory molecule expression. Further, prior to treatment, circulating non-classical and intermediate monocytes are more abundant by more than two-fold in complete responders to DC vaccination.

Accordingly, provided herein, in some aspects, are compositions for preparing dendritic cells for immunotherapy comprising (a) a sample of monocytes or monocyte progenitors in admixture with a cytokine preparation comprising one or more cytokines selected from the group consisting of macrophage colony-stimulating factor, TGF-$\beta$1, and MCP-1; and (b) a tissue culture medium.

In some embodiments of these aspects and all such aspects described herein, the sample of monocytes comprises circulating monocytes.

In some embodiments of these aspects and all such aspects described herein, the sample of monocytes or monocyte progenitors comprises bone marrow monocytes or monocyte progenitors.

In some embodiments of these aspects and all such aspects described herein, the incubation of the composition results in a population of monocytes enriched for non-classical and/or intermediate monocytes which, when differentiated to dendritic cells in vitro, provides dendritic cells with greater efficacy in a dendritic cell vaccine than dendritic cells produced from a non-enriched population of monocytes.

Also provided herein in some aspects are preparations of monocytes comprising at least 10% non-classical and/or intermediate monocytes, in admixture with one or more cytokines selected from the group consisting of macrophage colony-stimulating factor, TGF-$\beta$1, and MCP-1.

In some embodiments of these aspects and all such aspects described herein, the preparation further comprises a tissue culture medium.

In some embodiments of these aspects and all such aspects described herein, the preparation comprises at least 15% non-classical and/or intermediate monocytes.

In some aspects, provided herein, are pharmaceutical compositions for promoting patient responsiveness to immunotherapy comprising: (a) a population of dendritic cells prepared by in vitro differentiation of a population of monocytes enriched for non-classical and/or intermediate monocytes relative to the proportions of non-classical and/or intermediate monocytes occurring in vivo, where the dendritic cells express one or more co-stimulatory molecules at a level greater than that expressed by dendritic cells prepared by in vitro differentiation of a non-enriched monocyte population; and (b) a pharmaceutically acceptable excipient, diluent, and/or carrier.

In some embodiments of these aspects and all such aspects described herein, the non-classical monocytes were CD16$^+$ and CD14$^{dim}$/CD14$^-$ and the intermediate monocytes were CD16$^+$ and CD14$^+$ prior to their differentiation to dendritic cells.

In some embodiments of these aspects and all such aspects described herein, the immunotherapy comprises a cell-based, cytokine-based and/or antibody-based therapy.

In some embodiments of these aspects and all such aspects described herein, the cell-based immunotherapy comprises dendritic cell vaccination and/or adoptive T cell therapy.

In some embodiments of these aspects and all such aspects described herein, the immunotherapy comprises inhibition of an immune checkpoint.

In some embodiments of these aspects and all such aspects described herein, the inhibition of an immune checkpoint comprises inhibition of PD-1, PD-L1, TIM-3, CTLA4, LAG-3 and/or TIGIT.

In some embodiments of these aspects and all such aspects described herein, the inhibition comprises administering an antibody that binds to and inhibits a checkpoint regulator protein.

In some embodiments of these aspects and all such aspects described herein, the sample of monocytes comprises circulating monocytes.

In some embodiments of these aspects and all such aspects described herein, the sample of monocytes comprises bone marrow monocytes and/or monocyte progenitors.

In some embodiments of these aspects and all such aspects described herein, the one or more co-stimulatory molecules is selected from CD80, CD83, CD86, and MHC Class II or HLA-DR.

In some embodiments of these aspects and all such aspects described herein, the population of cells enriched for non-classical and/or intermediate monocytes is prepared by contacting a sample of monocytes or monocyte progenitors with one or more cytokines.

In some embodiments of these aspects and all such aspects described herein, the contacting promotes the transition of classical monocytes to an intermediate and/or non-classical phenotype.

In some embodiments of these aspects and all such aspects described herein, the one or more cytokines are selected from macrophage colony-stimulating factor, TGF-β1, and MCP-1.

In some embodiments of these aspects and all such aspects described herein, the population of cells enriched for non-classical and/or intermediate monocytes is prepared by a method comprising cell sorting. In some embodiments of these aspects and all such aspects described herein, the cell sorting comprises flow cytometric cell sorting, magnetic-bead based cell sorting, or a combination thereof.

In some embodiments of these aspects and all such aspects described herein, the sample of monocytes is isolated from a cancer patient.

In some embodiments of these aspects and all such aspects described herein, the non-classical and/or intermediate monocytes comprised at least 10% of the population of monocytes.

In some embodiments of these aspects and all such aspects described herein, the non-classical and/or intermediate monocytes comprised at least 15% of the population of monocytes.

In other aspects, provided herein are pharmaceutical compositions comprising: (a) a population of dendritic cells prepared by in vitro differentiation of a population of monocytes enriched for non-classical and/or intermediate monocytes relative to the proportions of non-classical and/or intermediate monocytes occurring in vivo, wherein said dendritic cells express one or more co-stimulatory molecules at a level greater than that expressed by dendritic cells prepared by in vitro differentiation of a non-enriched monocyte population; and (b) a pharmaceutically acceptable excipient, diluent, and/or carrier.

In some embodiments of these aspects and all such aspects described herein, the sample of monocytes comprises circulating monocytes.

In some embodiments of these aspects and all such aspects described herein, the sample of monocytes comprises bone marrow monocytes and/or monocyte progenitors.

In some embodiments of these aspects and all such aspects described herein, the dendritic cells derived from the non-classical and/or intermediate monocytes exhibit increased expression of one or more co-stimulatory molecules relative to a dendritic cell population derived from CD14$^+$CD16$^-$ monocytes.

In some embodiments of these aspects and all such aspects described herein, the one or more cytokines are selected from macrophage colony-stimulating factor, TGF-β1, and MCP-1.

In some embodiments of these aspects and all such aspects described herein, the one or more co-stimulatory molecule(s) is selected from CD80, CD83, CD86, and MHC Class II or HLA-DR.

In some embodiments of these aspects and all such aspects described herein, the population of cells enriched for non-classical and/or intermediate monocytes is prepared by a method comprising cell sorting.

In some embodiments of these aspects and all such aspects described herein, the cell sorting comprises flow cytometric cell sorting, magnetic-bead based cell sorting, or a combination thereof.

In some embodiments of these aspects and all such aspects described herein, the sample of monocytes is isolated from a cancer patient.

In some embodiments of these aspects and all such aspects described herein, the non-classical and/or intermediate monocytes comprise at least 10% of the population of cells. In some embodiments of these aspects and all such aspects described herein, the non-classical and/or intermediate monocytes comprise at least 15% of the population of cells.

Also provided herein, in some aspects, are methods to increase efficacy of an immunotherapy comprising: contacting a sample comprising monocytes with one or more cytokines that promote the transition of monocytes in the sample to a non-classical and/or intermediate phenotype and maturing the monocytes under conditions that permit said transition; where the matured monocytes are enriched for non-classical and/or intermediate monocytes relative to said sample of monocytes, where the population of non-classical monocytes is CD16$^+$ and CD14$^{dim}$/CD14$^-$ and the population of intermediate monocytes is CD16$^+$ and CD14$^+$; and where the enriched population permits enhanced efficacy of an immunotherapy when differentiated to dendritic cells.

In some embodiments of these aspects and all such aspects described herein, dendritic cells derived from the non-classical and/or intermediate monocytes have increased expression of one or more co-stimulatory molecules relative to a population of CD14$^+$CD16$^-$ monocytes.

In some embodiments of these aspects and all such aspects described herein, the one or more co-stimulatory molecules is selected from CD80, CD83, CD86, and MHC Class II or HLA-DR.

In some embodiments of these aspects and all such aspects described herein, the one or more cytokines comprises macrophage colony-stimulating factor, TGF-β1, and MCP-1.

In some embodiments of these aspects and all such aspects described herein, the method further comprises cell sorting. In some embodiments of these aspects and all such aspects described herein, the cell sorting comprises flow cytometric cell sorting, magnetic-bead based cell sorting, or a combination thereof.

In some embodiments of these aspects and all such aspects described herein, the sample of monocytes is isolated from a cancer patient.

In some embodiments of these aspects and all such aspects described herein, the sample of monocytes comprises circulating monocytes.

In some embodiments of these aspects and all such aspects described herein, the sample of monocytes comprises bone marrow monocytes or monocyte progenitors.

In some embodiments of these aspects and all such aspects described herein, the method further comprises culturing the enriched for non-classical and/or intermediate monocytes in a dendritic cell maturation cocktail.

In some embodiments of these aspects and all such aspects described herein, the immunotherapy comprises a dendritic cell vaccine.

In some aspects, provided herein are methods to increase efficacy of an immunotherapy comprising: (a) contacting a sample comprising monocytes or monocyte progenitors with one or more cytokines that promote the transition of monocytes in the sample to a non-classical and/or intermediate phenotype and maturing the monocytes under conditions that permit the differentiation; where the matured monocytes are enriched for non-classical and/or intermediate monocytes derived from the sample of monocytes, wherein the population of non-classical monocytes is CD16$^+$ and CD14$^{dim}$/CD14$^-$ and the population of intermediate monocytes is CD16$^-$ and CD14$^-$; and (b) culturing the enriched for non-classical and/or intermediate monocytes in a dendritic cell maturation cocktail to generate dendritic cells with enhanced efficacy in an immunotherapy.

In some embodiments of these aspects and all such aspects described herein, the dendritic cells derived from the non-classical and intermediate monocytes have increased expression of one or more co-stimulatory molecules relative to a population of CD14$^+$CD16$^-$ monocytes.

In some embodiments of these aspects and all such aspects described herein, the one or more co-stimulatory molecules is selected from CD80, CD83, CD86, and MHC Class II or HLA-DR.

In some embodiments of these aspects and all such aspects described herein, the one or more cytokines comprises macrophage colony-stimulating factor (m-CSF), TGF-β1, and MCP-1.

In some embodiments of these aspects and all such aspects described herein, the method further comprises enrichment by cell sorting. In some embodiments of these aspects and all such aspects described herein, the cell sorting comprises flow cytometric cell sorting, magnetic-bead based cell sorting, or a combination thereof.

In some embodiments of these aspects and all such aspects described herein, the sample of monocytes comprises circulating monocytes or bone-marrow monocytes or monocyte progenitors.

In some embodiments of these aspects and all such aspects described herein, the sample of monocytes is from a cancer patient.

In some embodiments of these aspects and all such aspects described herein, the immunotherapy comprises a dendritic cell vaccine or dendritic cell vaccination.

Provided herein in some aspects are methods of treatment of a subject having cancer, the methods comprising administering to the subject a dendritic cell vaccine comprising dendritic cells prepared from any of the compositions described herein or dendritic cells prepared using any of the methods described herein.

In some aspects, provided herein are methods of promoting patient responsiveness to immunotherapy comprising administering an agent that promotes the transition of classical monocytes to intermediate and/or non-classical monocyte phenotypes.

In some embodiments of these aspects and all such aspects described herein, the agent comprises one or more cytokines. In some embodiments of these aspects and all such aspects described herein, the cytokine(s) is/are selected from the group consisting of m-CSF, TGF-β1, and MCP-1.

In some embodiments of these aspects and all such aspects described herein, the immunotherapy comprises a cell-based, cytokine-based or antibody-based therapy.

In some embodiments of these aspects and all such aspects described herein, the cell-based immunotherapy comprises dendritic cell vaccination and/or adoptive T cell therapy.

In some embodiments of these aspects and all such aspects described herein, the immunotherapy comprises inhibition of an immune checkpoint. In some embodiments of these aspects and all such aspects described herein, the inhibition of an immune checkpoint comprises inhibition of PD-1, PD-L1, TIM-3, CTLA4, LAG-3 and/or TIGIT. In some embodiments of these aspects and all such aspects described herein, the inhibition comprises administering an antibody that binds to and inhibits a checkpoint regulator protein.

Also provided herein, in some aspects, are assays and methods for identifying a subject with increased responsiveness to dendritic cell therapy comprising: contacting a sample comprising monocytes obtained from a subject with an agent specific for CD16 and an agent specific for CD14; and analyzing expression of CD16 and CD14 on the monocytes of the contacted sample, such that if a population of CD16+ and CD14dim/CD14− and/or CD16+ and CD14+ cells comprises at least 10% of the monocytes in the sample, then the subject is determined to have increased responsiveness to dendritic cell therapy; and where if a population of CD16+ and CD14dim/CD14− and/or CD16+ and CD14+ cells comprises less than 10% of the monocytes in the sample, then the subject is determined to have decreased responsiveness to dendritic cell therapy.

In some embodiments of these aspects and all such aspects described herein, if the population of CD16+ and CD14dim/CD14− and/or CD16+ and CD14+ cells comprises less than 10% of the monocytes in the sample, the assay or method further comprises contacting a sample comprising monocytes from the subject with one or more cytokines that promote the transition of monocytes in the sample to a non-classical and/or intermediate phenotype and maturing the monocytes under conditions that permit said transition; and, in some embodiments, further enriching for non-classical and/or intermediate monocytes from the sample of monocytes, where the population of non-classical monocytes is CD16+ and CD14dim/CD14− and the population of intermediate monocytes is CD16+ and CD14+.

In some embodiments of these aspects and all such aspects described herein, the sample of monocytes comprises circulating monocytes or bone marrow monocytes or monocyte progenitors.

In some embodiments of these aspects and all such aspects described herein, dendritic cells derived from the non-classical and/or intermediate monocytes have increased expression of one or more co-stimulatory molecules relative to a population of CD14+CD16− monocytes. In some embodiments of these aspects and all such aspects described herein, the one or more co-stimulatory molecules is selected from CD80, CD83, CD86, and MHC Class II or HLA-DR.

In some embodiments of these aspects and all such aspects described herein, the one or more cytokines comprises macrophage colony-stimulating factor, TGF-β1, and MCP-1.

In some embodiments of these aspects and all such aspects described herein, the enriching comprises cell sorting. In some embodiments of these aspects and all such aspects described herein, the cell sorting comprises flow cytometric cell sorting, magnetic-bead based cell sorting, or a combination thereof.

In some embodiments of these aspects and all such aspects described herein, the sample comprising monocytes is isolated from a cancer patient.

In some embodiments of these aspects and all such aspects described herein, the assays and methods further comprise culturing the enriched non-classical and/or intermediate monocytes in a dendritic cell maturation cocktail.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The term "dendritic cells" or "DCs" refers to a diverse population of morphologically similar cell types found in a variety of lymphoid and non-lymphoid tissues (Steinman (1991) Ann. Rev. Immunol. 9:271-296). Dendritic cells constitute the most potent APCs in an organism. Dendritic cells can be generated by differentiation from monocytes, and possess a distinct phenotype from monocytes. "Immature DCs" are capable of capturing antigens by endocytosis, phagocytosis, macropinocytosis or adsorptive pinocytosis and receptor mediated antigen uptake, and are phenotypically CD80$^-$ or CD80$^{low}$, CD83$^-$ or CD8$^{low}$, CD86$^{low}$, and have high intracellular concentrations of MHC class II molecules (also referred to as HLA molecules in humans, (HLA-DP, HLA-DM, HLA-DOA, HLA-DOB, HLA-DQ, and HLA-DR). "Mature DCs" have a veiled morphology, a lower capacity for endocytosis and are phenotypically CD80$^{high}$, CD83$^{high}$, CD86$^{high}$ in comparison to immature DCs. Mature DCs secrete IL-12 p70 polypeptide or protein, and/or secrete significantly reduced levels (0 to 500 pg/ml per million DCs) of IL-10. IL-10 and IL-12 levels can be determined by ELISA of culture supernatants collected at up to 36 hrs post induction of DC maturation from immature DCs (Wierda W. G. et al (2000) Blood 96: 2917; Ajdary S et al (2000) Infection and Immunity 68: 1760. See Banchereau and Steinman (1998) Nature 392:245 for a review).

As used herein, "monocyte" refers to large CD14$^+$ or CD14$^{dim}$ leukocytes having the capacity, under certain in vitro conditions (e.g., incubation in a dendritic cell maturation cocktail, as described herein), to differentiate into a dendritic cell. Monocytes are produced by the bone marrow from precursors or "monocyte progenitors" called "monocyte-macrophage dendritic cell progenitors" (MDPs) or "monoblasts," which are bipotent cells that differentiate from hematopoietic stem cells. In some embodiments, hematopoietic stem cells are encompassed by the term "monocyte progenitor," as used herein. Monocytes present in the bloodstream are referred to herein as "circulating monocytes." As used herein, a "classical monocyte" refers to a monocyte characterized by high level expression of the CD14 cell surface receptor (CD14$^+$ CD16$^-$ monocyte), an "intermediate monocyte" refers to a monocyte characterized by high level expression of CD14 and medium-low level expression of CD16 (CD14$^+$CD16$^{+/lo}$ monocytes), and a "non-classical monocyte" refers to a monocyte characterized by low level expression of CD14, and expression of CD16 (CD14$^{lo/dim}$CD16$^+$ monocyte). Thus, interemediate and non-classical monocytes share the characteristic of CD16 expression, albeit to different degrees.

As used herein, examples of "samples of monocytes or monocyte progenitors" include bodily fluids known to comprise monocytes, such as blood and bone marrow fluid. The blood is collected from a living body (including, but not limited to, e.g., a human cancer patient), and examples thereof include peripheral blood and cord blood. In particular, peripheral blood is preferred from the viewpoint of reducing the burden on the subject. The body fluid can be collected by any method know in the art and can be collected from a region such as an arm, wrist, or foot using, for example, a syringe or winged needle. Samples of monocytes or monocyte progenitors for use in the compositions, assays, and methods described herein can be obtained from a number of sources including, but not limited to, blood, blood fractions (e.g., white blood cells (WBCs), buffy coats, peripheral blood mononuclear cells (PBMCs), etc, and as well as in compositions further enriched for monocytes.

As used herein, "leukapheresis" refers to a procedure by which the white blood cells are removed from a subject's blood, the remainder of which is then transfused back into the subject. The leukapheresis product is typically a blood fraction enriched for PBMCs, with low levels of contaminating red blood cells, granulocytes and platelets.

As used herein, a "cytokine preparation" refers to a composition comprising one or more cytokines that can be used to promote transition of one monocyte subset to another monocyte subset, or to a dendritic cell population. Such cytokine preparations can comprise one or more of macrophage colony-stimulating factor, TGF-β1, and MCP-1, which promote monocyte transition to intermediate and non-classical monocyte phenotypes. A dendritic cell maturation cocktail can include, e.g., IL-4 and GM-CSF, which promote differentiation of monocytes to immature dendritic cells in about 7 days in culture. A cocktail including TNF-α can be used to promote maturation of immature DCs to the mature DC phenotype. A preferred DC maturation cocktail includes, e.g., IL-6, IL-1β, TNF-α and prostaglandin $E_2$. Other cytokine treatment cocktails and protocols for promoting monocyte differentiation are known in the art, and/or commercially available—see, e.g., Dendritic Cell Generation Medium, PromoCell Catalog No. C-28050, PromoCell, Heidelberg, Germany. Amounts and ranges of cytokine concentrations for use in transitioning monocytes in a sample to a non-classical or intermediate phenotype or for promoting differentiation of monocytes to DCs differ according to the cytokine(s) being used.

As used herein, the terms "culture medium" or "tissue culture medium" encompass media in liquefied prepared forms and also component mixtures (usually powder) before preparation. Specifically, a culture medium can contain a nutritional component, a pH adjuster, and other components for enabling culture of monocytes. Examples of such tissue culture media include serum-free synthetic culture media for lymphocytes, AIM-V, and RPMI-1640. Culture media can also comprise reagents that are usually used in cell culture, such as antibiotics (e.g., gentamycin and kanamycin), albumin, and serum (e.g., fetal bovine serum). Serum-free medium can be supplemented with a serum-replacement composition of known or defined composition, thereby avoiding use of non-autologous serum.

The terms "isolate" and "methods of isolation," as used herein, refer to any process whereby a cell or population of cells, such as a population of monocytes, is removed from a subject or sample in which it was originally found, or from a descendant of such a cell or cells. The term "isolated population," as used herein, refers to a population of cells that has been removed and separated from a biological sample, or a mixed or heterogeneous population of cells found in such a sample. Such a mixed population includes, for example, a population of monocytes obtained from circulating blood. In some embodiments, an isolated population is a substantially pure population of cells as compared to the heterogeneous population from which the cells were isolated or enriched from. In some embodiments, an isolated cell or cell population, such as a population of monocytes, is further cultured in vitro or ex vivo, e.g., in the presence of growth factors or cytokines, to further expand the number of cells in the isolated cell population or substantially pure cell population or to promote differentiation to a particular cell or cell subtype(s), such as non-classical and/or intermediate monocytes. Such culture can be performed using any method known to one of skill in the art, for example, as described in the Examples section.

The term "substantially pure," with respect to a particular cell population, refers to a population of cells that is at least about 75%, at least about 80%, at least about 85%, at least about 90%, at least about 95%, at least about 98%, or at least about 99% pure, with respect to the cells making up a total cell population. In other words, the terms "substantially pure" or "essentially purified," with regard to a population of monocytes isolated for use in the methods disclosed herein, refers to a population of monocyte cells that contain fewer than about 25%, fewer than about 20%, fewer than about 15%, fewer than about 10%, fewer than about 9%, fewer than about 8%, fewer than about 7%, fewer than about 6%, fewer than about 5%, fewer than about 4%, fewer than about 3%, fewer than about 2%, fewer than about 1%, or less than 1%, of cells that are not monocytes, as defined by the terms herein.

The terms "enriching" or "enriched" are used interchangeably herein and mean that the yield (fraction) of cells of one type, such as non-classical monocytes and/or intermediate monocytes for use in the compositions and methods described herein, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, by at least 100%, by by at least 150%, by at least 200%, by at least 300%, by at least 400%, by at least 500%, by at least 750%, by 1000%, or more over the fraction of cells of that type in the starting sample, culture, or preparation. Alternatively, an enriched for population of non-classical monocytes and/or intermediate monocytes comprises at least 15%, at least 20%, at least 30%, at least 40%, at least 50%, at least 60%, at least 70%, at least 80%, at least 90%, at least 95%, at least 99%, or more of non-classical monocytes and/or intermediate monocytes relative to classical monocytes. Accordingly, a "population of monocytes enriched for non-classical and intermediate monocytes" obtained for use in the compositions and methods described herein is most preferably at least 200% enriched for non-classical and intermediate monocytes, or comprises at least 20% non-classical and intermediate monocytes.

As used herein, the phrase "dendritic cells with greater efficacy in a dendritic cell vaccine than dendritic cells produced from a non-enriched population of monocytes" refers to dendritic cells generated using the compositions and methods described herein that are generated from non-classical and/or intermediate monocyte subsets and have, for example, increased expression of one or more co-stimulatory molecules relative to dendritic cells not produced from non-classical and/or intermediate monocyte subsets.

As used herein, the term "immunotherapy" refers to the treatment of disease via the stimulation, induction, subversion, mimicry, enhancement, augmentation or any other modulation of a subject's immune system to elicit or amplify adaptive or innate immunity (actively or passively) against cancerous or otherwise harmful proteins, cells or tissues. Immunotherapies (i.e., immunotherapeutic agents) include cancer vaccines, immunomodulators, "antibody-based immunotherapies" or monoclonal antibodies (e.g., humanized monoclonal antibodies), immunostimulants, cell-based therapies such as adoptive T-cell therapies or dendritic cell immunotherapies or dendritic cell vaccines, and viral therapies, whether designed to treat existing cancers or prevent the development of cancers or for use in the adjuvant setting to reduce likelihood of recurrence of cancer.

"Adoptive T-cell therapies," as used herein include T-cell therapies in which T-cells are expanded in vitro using cell culture methods relying on the immunomodulatory action of interleukin-2 and returning these to the patient in large numbers intravenously in an activated state. Adoptive T-cell therapies can involve genetically engineering a subject's or patient's own T cells to produce recombinant receptors on their surface referred to as "chimeric antigen receptors" (CARs).

"Dendritic cell vaccination" refers to a form of immunotherapy designed to induce T cell-dependent immunity, such as cancer-specific T cell-dependent anti-tumor immunity, that can result in durable complete responses using DCs. Examples of "dendritic cell (DC) immunotherapies" or "dendritic cell vaccines," as used herein, include modified dendritic cells and any other antigen presenting cell, autologous or xeno, whether modified by multiple antigens, whole cancer cells, single antigens, by mRNA, phage display or any other modification, including but not restricted to ex vivo-generated, antigen-loaded dendritic cells (DCs) to induce antigen-specific T-cell immunity, ex vivo gene-loaded DCs to induce humoral immunity, ex vivo-generated, antigen-loaded DCs to induce tumour-specific immunity, ex vivo-generated immature DCs to induce tolerance, including, but not limited to, Provenge and others.

As used herein, the phrases "promoting patient responsiveness to immunotherapy" generally refers to increasing or enhancing a patient's or subject's response to a given immunotherapy as measured, for example, by a decrease in unwanted cellular proliferation; reduction in the number of cancer cells; reduction of tumor size; inhibition of (i.e., slow to some extent and preferably stop) cancer cell infiltration into peripheral organs; inhibition of (i.e., slow to some extent and preferably stop) tumor metastasis; inhibition of, to some extent, tumor growth; reduction of signaling in the target cells, and/or relief, to some extent, of one or more of the symptoms associated with the cancer. For the avoidance of any doubt, the terms "increasing or enhancing a patient's or subject's response to a given immunotherapy" refers to an increase, as compared to an untreated subject, of at least about 10%, of at least about 15%, of at least about 20%, of at least about 25%, of at least about 30%, of at least about 35%, of at least about 40%, of at least about 45%, of at least about 50%, of at least about 55%, of at least about 60%, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, at least about a 10-fold increase, at least about a 25-fold increase, at least about a 50-fold increase, at least about a 100-fold increase, or any increase of 100-fold or greater of one or more measurements of a patient's response.

As used herein, the phrase "increased responsiveness to immunotherapy" generally refers to a patient or subject in whom there is an increase or enhancement of the patient's or subject's response to a given immunotherapy as measured, for example, by a decrease in unwanted cellular proliferation; reduction in the number of cancer cells; reduction of tumor size; inhibition of (i.e., slow to some extent and preferably stop) cancer cell infiltration into peripheral organs; inhibition of (i.e., slow to some extent and preferably stop) tumor metastasis; inhibition of, to some extent, tumor growth; reduction of signaling in the target cells, and/or relief, to some extent, of one or more of the symptoms associated with the cancer. For the avoidance of any doubt, the phrase "increased or enhanced responsiveness to immunotherapy" refers to an increase, as compared to an untreated subject or subject who does not have increased percentages of non-classical or intermediate monocytes in a sample, of at least about 10%, of at least about 15%, of at least about 20%, of at least about 25%, of at least about 30%, of at least about 35%, of at least about 40%, of at least about 45%, of at least about 50%, of at least about 55%, of at least about 60%, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, at least about a 10-fold increase, at least about a 25-fold increase, at least about a 50-fold increase, at least about a 100-fold increase, or any increase of 100-fold or greater of one or more measurements of a patient's response.

As used herein, the phrase "therapeutically effective amount" refers to an amount of the immunotherapeutic or other active agent (drug, biologic, etc.) effective to treat a disease or disorder in a mammal. In the case of a malignancy, the therapeutically effective amount of the agent can reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce signaling in the target cells, and/or relieve, to some extent, one or more of the symptoms associated with the cancer.

As used herein, a "co-stimulatory molecule" refers to a cell-surface molecule on a dendritic cell that acts to provide a stimulatory signal to a T cell to activate T-cell dependent immune responses. Non-limiting examples of co-stimulatory molecules include CD80, CD83, CD86, MHC Class II, members of the B7-family of co-stimulatory molecules, CD40, CD40 ligand, CD30, CD30 ligand, 4-IBB receptor, 4-IBB ligand, CD27, FAS receptor, FAS ligand, TRAIL receptor, TRAIL ligand.

The terms "increased," "increase," "greater than," "enhance," or "expand" are all used herein to generally mean an increase in, for example, the number of non-classical and/or intermediate monocytes, the expression of one or more co-stimulatory molecules on a dendritic cell population generated using the compositions and methods described herein, by a statistically significant amount. For the avoidance of any doubt, the terms "increased," "increase," "expand," "expanded," "greater than," or "enhance" mean an increase, as compared to a reference level, of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, at least about a 10-fold increase, at least about a 25-fold increase, at least about a 50-fold increase, at least about a 100-fold increase, or any increase of 100-fold or greater, as compared to a control or reference level. A control sample or control level is used herein to describe a population of cells obtained from the same biological source that has, for example, not been treated using the compositions and methods described herein, or refers to a sample or level prior to treatment/administration with the compositions and methods described herein.

The phrases "dendritic cells express one or more co-stimulatory molecules at a level greater than that expressed by dendritic cells prepared by in vitro differentiation of a non-enriched monocyte population" or "increased expression of one or more co-stimulatory molecules relative to a population of dendritic cells derived from $CD14^+CD16^-$ monocytes" refer to a population of dendritic cells prepared by in vitro differentiation from an enriched for population of non-classical and/or intermediate monocytes using any of the compositions, assays, and methods described herein in which the level or expression of one or more co-stimulatory molecules is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, at least about a 10-fold increase, at least about a 25-fold increase, at least about a 50-fold increase, at least about a 100-fold increase, or any increase of 100-fold or greater, than that in a population of dendritic cells prepared by in vitro differentiation from a population of monocytes in which no enrichment has been performed.

The term "immune checkpoint," as used herein, refer to a group of molecules expressed by T cells that effectively serve as "brakes" to down-modulate or inhibit an immune response. Immune checkpoint molecules include, but are not limited to Programmed Death 1 (PD-1, also known as PDCD1 or CD279), Cytotoxic T-Lymphocyte Antigen 4 (CTLA-4), LAG3 (also known as CD223), TIM3 (also known as HAVCR2), BTLA (also known as CD272), BY55 (also known as CD160), TIGIT (also known as VSTM3), B7H5 (also known as C10orf54), LAIR1 (also known as CD305), SIGLEC10, and 2B4 (also known as CD244), which directly inhibit immune cells.

The terms "decrease," "inhibit," "reduce" and variations thereof are all used herein to generally mean to cause an overall decrease an increase in, for example, the number or percentage of classical monocytes in a sample, or the number or degree of one or more of the symptoms associated with the cancer by a statistically significant amount. For the avoidance of any doubt, the terms "decrease," "inhibit," "reduce" and variations thereof mean a decrease, as compared to a reference level, of at least preferably of 10% or greater, 15% or greater, 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter, such as expression of one or more cell-surface molecules, or symptoms. Reduce or inhibit can refer to, for example, the symptoms of the disorder being treated, the presence or size of metastases or micrometastases, the size of the primary tumor, the presence or the size of the dormant tumor, etc.

"Cell sorting," as used herein, encompasses typically immunological-based methods of positive and negative selection, which result in the physical isolation of a cell type, such as a monocyte subset, having a specific cell surface marker or combination of markers using an antibody or an antibody fragment, or a combination of antibodies or antibody fragments, which specifically recognize(s) the marker(s). Examples include, but are not limited to cell sorting by fluorescence-activated cell sorting (FACS), magnetic beads [Magnetic-activated cell sorting (MACS)], columns-based cell sorting, and immunopanning.

As defined herein, "positive selection" refers to techniques that result in the isolation or enrichment of cells expressing specific cell-surface markers, while "negative selection" refers techniques that result in the isolation or enrichment of cells not expressing specific cell-surface markers.

"Magnetic bead-based sorting methods" refer to affinity methods using antibodies labeled to magnetic beads, biodegradable beads, and/or non-biodegradable beads, and any combination of such methods.

As defined herein, "flow cytometry" refers to a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters.

As defined herein, "fluorescence-activated cell sorting" or "flow cytometric based sorting" methods refer to flow cytometric methods for sorting a heterogeneous mixture of cells from a single biological sample into one or more containers, one cell at a time, based upon the specific light scattering and fluorescent characteristics of each cell and provides fast, objective and quantitative recording of fluorescent signals from individual cells as well as physical separation of cells of particular interest.

A "tumor" as used herein refers to an uncontrolled growth of cells which can interfere with the normal functioning of the bodily organs and systems. A "cancer" is an uncontrolled growth or proliferation of cells that has gained the ability for at least some of its cells to leave the primary site of growth amd seed other tissues or organs, i.e., the ability to metastasize, as the term is used herein. A patient subject that has a cancer or a tumor, i.e., a cancer or tumor patient, is a subject having objectively measurable cancer (metastasized) or tumor cells present in the subject's body. Included in the definition of a tumor are benign and malignant tumors, as well as dormant tumors or micrometastases. Examples of cancer encompassed within the term include, but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NEIL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), tumors of primitive origins and Meigs' syndrome. By "metastasis" is meant the spread of cancer from its primary site to other places in the body.

The terms "subject," "patient," and "individual" as used in regard to any of the compositions, assays, and methods described herein are used interchangeably herein, and refer to an animal, for example a human, recipient of the compositions and methods described herein, or from whom a sample comprising monocytes is obtained. For diagnosis and/or treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates.

As used herein, the phrase "alleviating a symptom of a cancer or tumor" is ameliorating any condition or symptom associated with the cancer such as the symptoms of the cancer being treated, the presence or size of metastases or micrometastases, the size of the primary tumor, the presence or the size of the dormant tumor, etc. As compared with an equivalent untreated control, such as a subject prior to the use of the compositions and methods described herein, such reduction or degree of prevention is at least 5%, 10%, 20%, 40%, 50%, 60%, 80%, 90%, 95%, or more as measured by any standard technique known to one of ordinary skill in the art. A patient or subject who is being treated for a cancer or tumor is one who a medical practitioner has diagnosed as having such a condition. Diagnosis can be by any suitable means.

As used herein, in regard to any of the compositions, methods, and uses described herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "effective amount" as used herein refers to the amount of dendritic cells generated using the compositions and methods described herein, needed to alleviate at least one or more symptom of the disease or disorder being treated, and relates to a sufficient amount of pharmacological composition to provide the desired effect. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

As used herein, "CD14" refers to the cell-surface receptor form of the CD14 molecule which is anchored to the cell membrane by a glycosylphosphatidylinositol tail, and acts as a co-receptor (along with the Toll-like receptor TLR 4 and MD-2) for the detection of bacterial lipopolysaccharide (LPS).

As used herein, "CD16" refers to the cell-surface Fc receptors FcγRIIIa (CD16a) and FcγRIIIb (CD16b). These receptors bind to the Fc portion of IgG antibodies which then activates the NK cell for antibody-dependent cell-mediated cytotoxicity.

A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analaysis of such a contacted cell to determine whether the antibody is bound the cell. A cell is considered "dim" or "low" for a cell-surface marker if it expresses the marker on its cell-surface in amounts sufficient to be detected using methods known to those of skill in the art, such as contacting a cell with an antibody that binds specifically to that marker, and subsequently performing flow cytometric analaysis of such a contacted cell to determine whether the antibody is bound the cell, but there exists another distinct population of cells that expresses the marker at a higher level, giving rise to at least two populations that are distinguishable when analyzed using, for example, flow cytometry. Similarly, a cell is considered "negative" for a cell-surface marker if it does not express the marker on its cell-surface in amounts sufficient to be detected using methods known to those of skill in the art, such as contacting a cell with an antibody that binds specifically to that marker and subsequently performing flow cytometric analaysis of such a contacted cell to determine whether the antibody is bound to the cell.

As used herein, an "agent specific for" a particular cell-surface biomarker, such as CD14 or CD16, refers to an agent that can selectively react with or bind to that cell-surface marker, but has little or no detectable reactivity to other cell-surface markers or antigens. Agents specific for cell-surface molecules can include, but are not limited to, antibodies or antigen-binding fragments thereof, natural or recombinant ligands, small molecules, nucleic acid sequences that specifically bind a given target (e.g., aptamers), and nucleic acid analogues; intrabodies; and other proteins or peptides.

As used herein, the term "antibody" refers to an intact immunoglobulin or to an antigen-binding fragment thereof. An antibody can be polyclonal or monoclonal. Antigen-binding fragments may be produced by recombinant DNA techniques or by enzymatic or chemical cleavage of intact antibodies. "Antigen-binding fragments" include, inter alia, Fab, Fab', F(ab')2, Fv, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)].

As used herein, the terms "label" or "tag refer to a composition capable of producing a detectable signal indicative of the presence of a target, such as, the presence of a specific cell-surface marker in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the assays and methods described herein.

The terms "labeled antibody" or "tagged antibody", as used herein, includes antibodies that are labeled by detectable means and include, but are not limited to, antibodies that are fluorescently, enzymatically, radioactively, and chemiluminescently labeled. Antibodies can also be labeled with a detectable peptide tag, such as c-Myc, HA, VSV-G, HSV, FLAG, V5, or HIS, which can be detected using an antibody specific to the tag, for example, an anti-c-Myc antibody.

DETAILED DESCRIPTION

Figure 1:
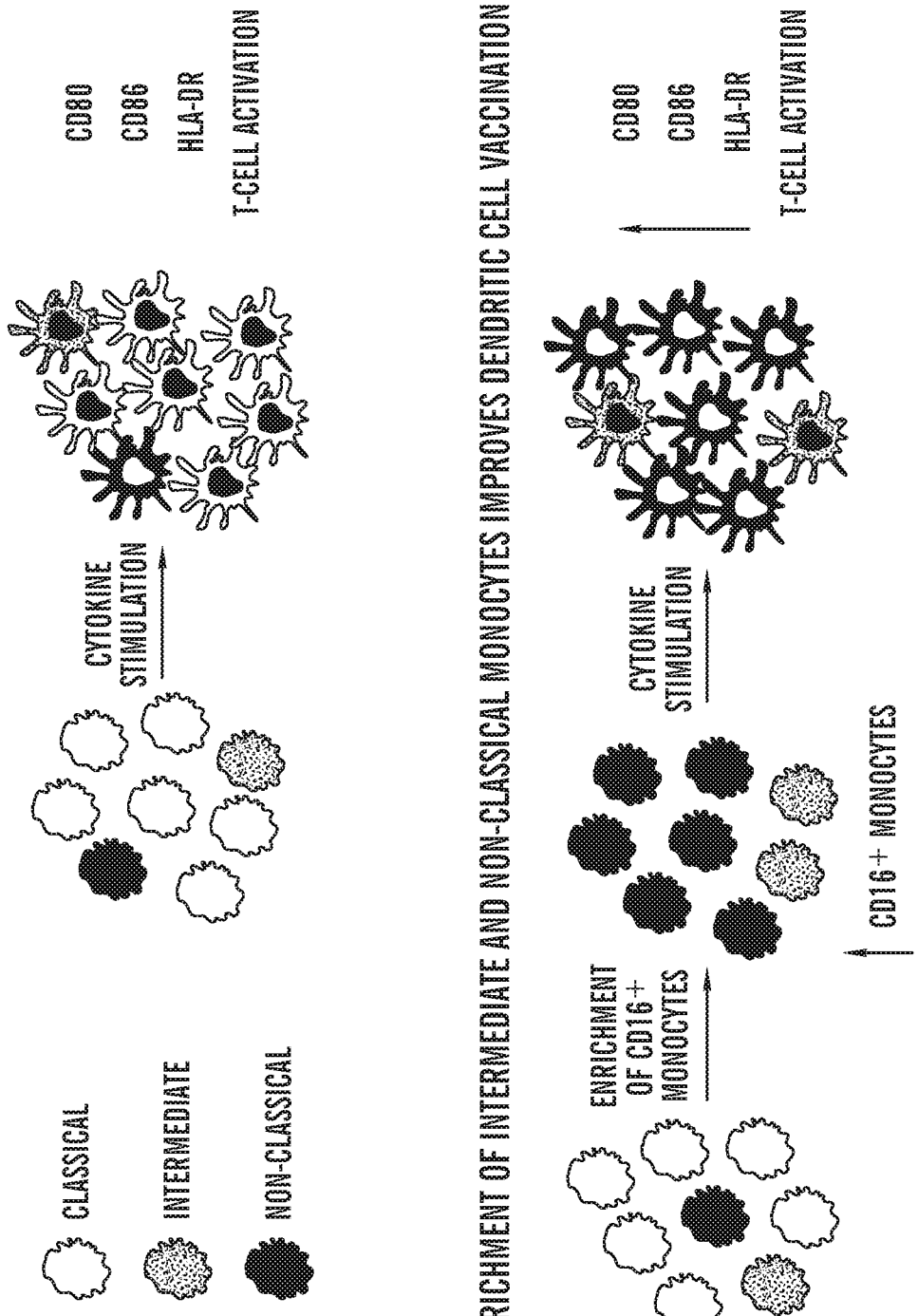
FIG. 1 shows that enrichment of non-classical monocytes prior to dendritic cell maturation increases T cell activation. Conventional DC protocols utilize mostly classical monocytes as starting material for DC culture (top). As described herein, an increased percentage of intermediate or non-classical monocytes results in superior DC product for dendritic cell vaccination. Utilization of DC with increased costimulatory molecule expression (CD80, CD86, HLA-DR) enhances anti-tumor immunity and improves patient responses to DC vaccination.

Compositions and methods are provided herein that relate to the discoveries described herein that intermediate (CD14$^+$ CD16$^+$), and non-classical (CD14$^{dim}$CD16$^+$) monocytes are increased more than two-fold in patients who later had complete responses to dendritic cell therapy. The findings described herein demonstrate that dendritic cells (DCs) derived from intermediate and non-classical monocytes have increased expression of costimulatory molecules important for T cell activation and lead to improved efficacy of vaccines by promoting T cell-dependent anti-tumor responses. To increase costimulatory molecule expression on monocyte-derived dendritic cells, provided herein are compositions and methods for converting the predominant circulating classical monocytes to a non-classical monocyte phenotype through cytokine stimulation via, for example, macrophage colony-stimulating factor. Once cultured into dendritic cells, these intermediate and non-classical monocyte derived cells have increased capacity to stimulate T cell proliferation. Accordingly, the compositions and methods described herein are useful for all dendritic cell vaccines that originate from monocytes.

In addition, assays and diagnostic and theranostic methods are provided herein that relate to the discoveries described herein that, prior to treatment, intermediate (CD14+CD16+), and non-classical (CD14dimCD16+) monocytes are increased more than two-fold in patients who later had complete responses to dendritic cell therapy or DC vaccination.

Dendritic cell vaccination is a form of immunotherapy designed to induce T cell-dependent immunity, such as cancer-specific T cell-dependent anti-tumor immunity, that can result in durable complete responses using DCs. Dendritic cells are specialized antigen presenting cells (APCs) that integrate a variety of incoming signals to orchestrate adaptive immune responses. Dendritic cells are a diverse population of morphologically similar cell types found in a variety of lymphoid and non-lymphoid tissues and are the most potent APCs in an organism. Dendritic cells can be generated, in vivo and in vitro, by differentiation from monocytes, and possess a distinct phenotype from monocytes. For example, a particular differentiating marker, CD14 antigen, is not found in dendritic cells but is possessed by monocytes. Mature DCs can provide all the signals necessary for T cell activation and proliferation. Also, mature dendritic cells are not phagocytic, whereas the monocytes and immature dendritic cells are strongly phagocytosing cells. Immature DCs are capable of capturing antigens by endocytosis, phagocytosis, macropinocytosis or adsorptive pinocytosis and receptor mediated antigen uptake, and are phenotypically CD80$^-$ or CD80$^{low}$, CD83$^-$ or CD8$^{low}$, CD86$^{low}$, and have high intracellular concentrations of MHC class II molecules. Mature DCs have a veiled morphology, a lower capacity for endocytosis and are phenotypically CD80$^{high}$, CD83$^{high}$, CD86$^{high}$ in comparison to immature DCs. Mature DCs secrete IL-12 p70 polypeptide or protein, and/or secrete significantly reduced levels (0 to 500 pg/ml per million DCs) of IL-10. IL-10 and IL-12 levels can be determined by ELISA of culture supernatants collected at up to 36 hrs post induction of DC maturation from immature DCs (Wierda W. G. et al (2000) Blood 96: 2917; Ajdary S et al (2000) Infection and Immunity 68: 1760. See Banchereau and Steinman (1998) Nature 392:245 for a review).

The goal of DC-based cancer immunotherapy is to use DCs to prime specific antitumor immunity through the generation of effector cells, typically T cells, which attack and lyse tumors. Such DC-based cancer immunotherapies or dendritic cell vaccines are mostly dependent on the generation of antigen-specific CD8+ T cells that generate cytotoxic T lymphocytes (CTLs) to reject cancer or infected cells. DC-based cancer immunotherapies act as therapeutic vaccines by priming naive T cells and modulating existing memory T cells. In addition, vaccination should lead to the generation of long-lived memory CD8+ T cells that will act to prevent relapse (K. Palucka and J. Banchereau, Immunity 39, 2013).

In particular, the desired properties of vaccine-elicited CD8+ T cells associated with the rejection of cancer include, in part, (1) high T cell receptor (TCR) affinity and high T cell avidity for peptide major histocompatibility complexes (MHCs) expressed on tumor cells, (2) high amounts of granzymes and perforin, (3) expression of surface molecules that allow T cell trafficking into the tumor (e.g., CXCR3) and persistence in the tumor site (e.g., integrins CD103 and CD49a), and (4) high expression of costimulatory molecules (e.g., CD80, CD83, CD86, CD137) or low expression of inhibitory molecules (e.g., cytotoxic T lymphocyte antigen 4 or PD-1).

A critical step in DC vaccination is the efficient presentation of cancer antigens to T cells. DCs are an essential component of vaccination through their capacity to capture, process, and present antigens to T cells. Activated (mature), antigen-loaded DCs initiate the differentiation of antigen-specific T cells into effector T cells that display unique functions and cytokine profiles. "DC maturation" refers to the differentiation of DCs from an immature phenotype to a mature phenotype and is associated with a wide variety of cellular changes, including (1) decreased antigen-capture activity, (2) increased expression of surface MHC class II molecules and costimulatory molecules, (3) acquisition of chemokine receptors (e.g., CCR7), which guide their migration, and (4) the ability to secrete different cytokines (e.g., interleukin-12 [IL-12]) that control T cell differentiation.

Three cell-surface markers characterize human blood DCs: CD303, expressed on plasmacytoid DCs (pDCs), and CD1c and CD141, both expressed on circulating DCs. Both CD1c+ and CD141+ DCs can produce IL-12, thereby enabling the generation of interferon-γ (IFN-γ)-secreting type 1 CD4+ T (Th1) cells and the priming of naive CD8+ T cells. Both CD1c+ and CD141+ DCs, isolated from blood or tissues, are able to cross-present long peptides of melanoma-tissue-derived antigen (MART-1) to T cell lines and acquire viral antigens and drive antiviral effector CD8+ T cell responses. However, they also display unique features. CD141+ CD1c-DCs, the human counterpart of mouse CD8a+ DCs, produce very large amounts of IFN-α upon recognition of synthetic double-stranded RNA and, when activated with poly I:C, efficiently cross-prime CD8+ T cells. CD1c+ DCs from both blood and lungs are uniquely able to drive the differentiation of CD103+ CD8+ mucosal T cells with high retention capacity in the lungs.

DCs can be exploited for vaccination against cancer through various means, including (1) nontargeted peptide- or protein and nucleic-acid-based vaccines captured by DCs in vivo, (2) vaccines composed of antigens directly coupled to DC antibodies, or (3) vaccines composed of ex-vivo-generated DCs that are loaded with antigens, any and all of which can be enhanced using the compositions and methods described herein.

A common method for preparing dendritic cells (DCs) for DC-based vaccination immunotherapies is to collect peripheral or circulating blood mononuclear cells (PBMCs) from a subject, and then ex vivo differentiate the monocytes, which are a small proportion of the PBMCs, into DCs, thereby generating "monocyte-derived DCs" ex vivo.

As demonstrated herein, prior to treatment, intermediate (CD14+CD16+) and non-classical (CD14dimCD16+) monocytes are increased more than two-fold in patients who later had complete responses to dendritic cell therapy. The findings described herein demonstrate that dendritic cells derived from non-classical monocytes, also referred to herein as "non-classical monocyte DCs" have increased expression of molecules important for T cell activation and lead to improved efficacy of vaccines by promoting T cell-dependent anti-tumor responses. To increase costimulatory molecule expression on monocyte-derived dendritic cells, provided herein are compositions and methods for converting the predominant circulating classical monocytes to a non-classical monocyte phenotype through cytokine stimulation via, for example, macrophage colony-stimulating factor. Once cultured into dendritic cells, these non-classical monocyte derived cells have increased costimulatory molecule expression, which leads to improved immune and clinical responses in cancer patients receiving dendritic cell vaccination. Accordingly, the compositions and methods described herein are useful for all dendritic cell vaccines that originate from monocytes.

In addition, provided herein are assays and methods for identifying cancer patients that are capable of having complete and durable responses to dendritic cell vaccination, prior to dendritic cell vaccination treatment, as well as theranostic assays for identifying and subsequently treating these patients and patients whose monocyte profile does not indicate a strong likelihood of DC vaccine therapeutic success.

Accordingly, provided herein, in some aspects are compositions for preparing dendritic cells for immunotherapy, such compositions comprising: (a) a sample of monocytes or monocyte progenitors in admixture with a cytokine preparation comprising one or more cytokines selected from the group consisting of macrophage colony-stimulating factor, TGF-β1, and MCP-1; and (b) a tissue culture medium.

In some embodiments of these aspects and all such aspects described herein, the sample of monocytes comprises circulating monocytes.

In some embodiments of these aspects and all such aspects described herein, the sample of monocytes or monocyte progenitors comprises bone marrow monocytes or monocyte progenitors, such as, for example, monoblasts or hematopoietic stem cells.

Monocytes are large $CD14^+$ or $CD14^{dim}$ leukocyte having the capacity, under certain in vitro conditions (e.g., incubation in a dendritic cell maturation cocktail, as described herein), to differentiate into a dendritic cell. Monocytes are produced by the bone marrow from monocyte-macrophage dendritic cell progenitors (MDPs) or monoblasts, which are bipotent cells that differentiate from hematopoietic stem cells. In some embodiments, a monocyte progenitor can also be a hematopoietic stem cell. Monocytes circulate in the bloodstream for about one to three days, and then typically move into tissues throughout the body. Monocytes present in the bloodstream are referred to as circulating monocytes. Monocytes that migrate from the bloodstream to other tissues differentiate into tissue resident macrophages or dendritic cells. Circulating human and mouse monocytes are broadly classified on the basis of surface receptor markers and biological responses into three subtypes. Based on the recently approved nomenclature by the Nomenclature Committee of the International Union of Immunological Societies (Ziegler-Heitbrock et al., 2010) human monocyte subtypes are categorized into "classical," "intermediate," and "non-classical" subtypes based on expression of CD14 and CD16 (FcγIII receptor). Classical monocytes comprise ~90% of total circulating monocytes in healthy donors, intermediate monocytes comprise ||5% of total circulating monocytes in healthy donors, and non-classical monocytes comprise ~5% of total circulating monocytes in healthy donors. As used herein, a "classical monocyte" refers to a monocyte characterized by high level expression of the CD14 cell surface receptor (CD14+ CD16− monocyte), an "intermediate monocyte" refers to a monocyte characterized by high level expression of CD14 and medium-low level expression of CD16 (CD14+CD16+ monocytes), and a "non-classical monocyte" refers to a monocyte characterized by low level expression of CD14 and expression of CD16 (CD14lo/dimCD16+ monocyte). Measurement of levels of expression of CD14 and CD16 for classification of monocyte subsets is typically performed by flow cytometry, as understood by one of ordinary skill in the art, according to standard practice.

Sources of monocytes or monocyte progenitors include, for example, bodily fluids known to comprise monocytes, such as blood and bone marrow fluid. The blood is collected from a living body (including, but not limited to, e.g., a human cancer patient), and examples thereof include peripheral blood and cord blood. In particular, peripheral blood is preferred from the viewpoint of reducing the burden on the subject. The body fluid can be collected by any method know in the art and can be collected from a region such as an arm, wrist, or foot using, for example, a syringe or winged needle.

Samples of monocytes or monocyte progenitors for use in the compositions, assays, and methods described herein can be obtained from a number of sources including, but not limited to, blood, blood fractions (e.g., white blood cells (WBCs), buffy coats, peripheral blood mononuclear cells (PBMCs), etc, and as well as in compositions further enriched for monocytes. In some embodiments, the monocytes are provided together with other PBMCs, for example, as a leukapheresis product. In another embodiment, the monocytes are enriched from PBMCs, or isolated directly from peripheral blood. Methods of isolating monocytes or PBMCs containing monocytes are known to those of skill in the art. In some embodiments, the monocytes are collected together with other PBMCs by leukapheresis. Methods of leukapheresis are known in the art. In some embodiments, PBMCs comprising monocytes are collected from a subject by leukapheresis at a hospital, clinic, doctor's office, etc. As used herein, "leukapheresis" refers to a procedure by which the white blood cells are removed from a subject's blood, the remainder of which is then transfused back into the subject. The leukapheresis product is typically a blood fraction enriched for PBMCs, with low levels of contaminating red blood cells, granulocytes and platelets. Methods and equipment for performing leukapheresis are well known in the art. Examples of leukapheresis apparatuses include the COBE-SPECTRA™ manufactured by GAMBRO BCT, and the CS3000 Plus Blood Cell Separator manufactured by Baxter Fenwal.

Cytokine preparations can be used to promote transition of a monocyte subset to another monocyte subset or differentiatioin of a monocyte to a dendritic cell, for example. Such cytokine preparations can comprise one or more of macrophage colony-stimulating factor, TGF-β1, and MCP-1, e.g., for promoting transition of classical monocytes to intermediate and/or non-classical monocyte phenotypes. A dendritic cell maturation cocktail can include, e.g., IL-4 and GM-CSF, which promote differentiation of monocytes to immature dendritic cells in about 7 days in culture. A cocktail including TNF-α can be used to promote maturation of immature DCs to the mature DC phenotype. A preferred DC maturation cocktail includes, e.g., IL-6, IL-1β, TNF-α and prostaglandin $E_2$. Other cytokine treatment cocktails and protocols for promoting monocyte differentiation are known in the art, and/or commercially available—see, e.g., Dendritic Cell Generation Medium, PromoCell Catalog No. C-28050, PromoCell, Heidelberg, Germany.

Amounts and ranges of cytokine concentrations for use in transitioning monocytes in a sample to a non-classical or intermediate phenotype or for promoting differentiation of monocytes to DCs differ according to the cytokine(s) being used. For example, macrophage colony-stimulating factor, TGF-β1, and MCP-1 can each be used at a concentration of 10 ng/ml, 20 ng/ml, 30 ng/ml, 40 ng/ml, 50 ng/ml, 60 mg/ml, 70 ng/ml, 80 ng/ml, 90 ng/ml, and 100 mg/ml, or in a range of 5-200 ng/ml or 10-100 ng/ml.

As used herein, the terms "culture medium" or "tissue culture medium" encompass media in liquefied prepared forms and also component mixtures (usually powder) before preparation. Specifically, a culture medium can contain a nutritional component, a pH adjuster, and other components for enabling culture of monocytes. Examples of such tissue culture media include serum-free synthetic culture media for lymphocytes, AIM-V, and RPMI-1640. Culture media can also comprise reagents that are usually used in cell culture, such as antibiotics (e.g., gentamycin and kanamycin), albumin, and serum (e.g., fetal bovine serum). In some embodiments of the aspects described herein, a tissue culture medium can comprise autologous plasma (i.e., the monocytes to be differentiated and the autologous plasma are collected from the same body). Serum-free medium can be supplemented with a serum-replacement composition of known or defined composition, thereby avoiding use of non-autologous serum. An exemplary tissue culture medium for the compositions and methods described herein is AIM-V serum-free medium, comprising cytokines as appropriate for monocyte transition, monocyte differentiation, or DC treatment with tumor antigen. As but one example, medium for DC treatment with tumor antigen can include AIM-V serum-free medium supplemented with, 20 ng/mL IL-4 (R & D Systems), tumor lysate or antigen (1-3 tumor cell equivalents per DC), and 50 ng/mL tumor necrosis factor a (R & D Systems). In some embodiments of the aspects described herein, a culture medium is serum-free. In some embodiments of the aspects described herein, a culture medium is supplemented with autologous serum.

In some embodiments of these aspects and all such aspects described herein, incubation of said composition results in a population of monocytes enriched for non-classical and intermediate monocytes which, when differentiated to dendritic cells in vitro, provides dendritic cells with greater efficacy in a dendritic cell vaccine than dendritic cells produced from a non-enriched population of monocytes.

Monocytes can be isolated by any process or method that removes a population of monocytes from a subject or sample in which it was originally found, or from a descendant of such a cell or cells. An isolated population of monocytes can be prepared using cells removed and separated from a biological sample, or from a mixed or heterogeneous population of cells found in such a sample. Such a mixed population includes, for example, a population of monocytes obtained from circulating blood. In some embodiments, an isolated population is a substantially pure population of cells as compared to the heterogeneous population from which the cells were isolated or enriched. In some embodiments, an isolated cell or cell population, such as a population of monocytes, is further cultured in vitro or ex vivo, e.g., in the presence of growth factors or cytokines, to further expand the number of cells in the isolated cell population or substantially pure cell population or to promote differentiation to a particular cell or cell subtype(s), such as non-classical and/or intermediate monocytes. Such culture can be performed using any method known to one of skill in the art, for example, including, but not limited to those described in the Examples section herein.

The proportion of non-classical and intermediate monocytes can be "enriched" in a sample or preparation as that term is defined herein, for use in the compositions, methods, and assays described herein. Accordingly, a "population of monocytes enriched for non-classical and intermediate monocytes" obtained for use in the compositions, assays, and methods described herein is most preferably at least 200% enriched for non-classical and intermediate monocytes, relative to their occurrence in a non-enriched sample or preparation, e.g., a non-enriched sample of peripheral blood, or comprises at least 20% non-classical and intermediate monocytes.

Dendritic cells prepared from a population of monocytes with greater or equal to 10% non-classical or intermediate monocytes will have greater efficacy in a dendritic cell vaccine than dendritic cells produced from a population or preparation of with less than 10% non-classical or intermediate monocytes. Similarly, DCs prepared from a population enriched for non-classical or intermediate monocytes, e.g., having at least 20% of such monocytes, will have greater efficacy in a dendritic cell vaccine. DCs produced from such populations have, for example, increased expression of one or more co-stimulatory molecules relative to dendritic cells not produced from enriched or isolated non-classical and/or intermediate monocyte subsets.

Also provided herein, in some aspects, are preparations of monocytes comprising at least 10% non-classical and/or intermediate monocytes, in admixture with one or more cytokines selected from the group consisting of macrophage colony-stimulating factor, TGF-β1, and MCP-1.

In some embodiments of these aspects and all such aspects described herein, the preparation further comprises a tissue culture medium.

In some embodiments of these aspects and all such aspects described herein, the preparation comprises at least 15% non-classical and/or intermediate monocytes.

The compositions and methods described herein provide, in part, monocyte preparations in which the non-classical and/or intermediate populations comprise a greater proportion of the total monocyte population than is typically found in a healthy individual, and recapitulates the proportions of non-classical and/or intermediate populations found in patients who had complete responses to DC immunotherapies prior to their DC immunotherapy treatment. Accordingly, in some embodiments of the aspects described herein, a preparation of monocytes comprises at least 15%, at least 20%, at least 30%, at least 40%, at least 50%, at least 60%, at least 70%, at least 80%, at least 90%, at least 95%, at least 99%, or more of non-classical monocytes and/or intermediate monocytes relative to classical monocytes.

Also provided herein, in some aspects, are pharmaceutical compositions for promoting patient responsiveness to immunotherapy, the compositions comprising: (a) a population of dendritic cells prepared by in vitro differentiation of a population of monocytes enriched for non-classical and intermediate monocytes relative to the proportions of non-classical and intermediate monocytes occurring in vivo, wherein said dendritic cells express one or more co-stimulatory molecules at a level greater than that expressed by dendritic cells prepared by in vitro differentiation of a non-enriched monocyte population; and (b) a pharmaceutically acceptable excipient, diluent, and/or carrier.

In some aspects, provided herein are pharmaceutical compositions comprising: (a) a population of dendritic cells prepared by in vitro differentiation of a population of monocytes enriched for non-classical and intermediate monocytes relative to the proportions of non-classical and intermediate monocytes occurring in vivo, wherein said dendritic cells express one or more co-stimulatory molecules at a level greater than that expressed by dendritic cells prepared by in vitro differentiation of a non-enriched monocyte population; and (b) a pharmaceutically acceptable excipient, diluent, and/or carrier.

In some embodiments of these aspects and all such aspects described herein, immunotherapy comprises a cell-based, cytokine-based and/or antibody-based therapy. In some embodiments of these aspects and all such aspects described herein, the cell-based immunotherapy comprises dendritic cell vaccination and/or adoptive T cell therapy.

Immunotherapy treats disease via the stimulation, induction, subversion, mimicry, enhancement, augmentation or any other modulation of a subject's immune system, to elicit or amplify adaptive or innate immunity (actively or passively) against cancerous or otherwise harmful proteins, cells or tissues. Immunotherapeutic agents include cancer vaccines, immunomodulators, antibody-based immunotherapies or monoclonal antibodies (including, but not limited to, humanized monoclonal antibodies), immunostimulants, cell-based therapies such as adoptive T-cell therapies or dendritic cell immunotherapies or dendritic cell vaccines, and viral therapies, whether designed to treat existing cancers or prevent the development of cancers or for use in the adjuvant setting to reduce likelihood of recurrence of cancer.

Examples of cancer vaccines include GVAX, Stimuvax, DCVax and other vaccines designed to elicit immune responses to tumor and other antigens including MUC1, NY-ESO-1, MAGE, p53 and others.

Examples of immunomodulators include 1MT, Ipilimumab, Tremelimumab and/or any drug designed to de-repress or otherwise modulate cytotoxic or other T cell activity against tumor or other antigens, including, but not restricted to, treatments that modulate T-Reg cell control pathways via CTLA-4, CD80, CD86, MHC (also referred to in humans as HLA, such as HLA-DR), B7-DC, B7-H1, B7-H2, B7-H3, B7-H4, CD28, other TCRs, PD-1, PDL-1, CD80, ICOS and their ligands, LAG, and TIM family members, whether via blockade, agonist or antagonist.

Examples of immunostimulants include corticosteroids and any other anti- or pro-inflammatory agent, steroidal or non-steroidal, including, but not restricted to, GM-CSF, interleukins (eg IL-2, IL-7, IL-12), cytokines such as the interferons, and others.

Examples of adoptive T-cell therapies include T-cell therapies in which T-cells are expanded in vitro using cell culture methods relying on the immunomodulatory action of interleukin-2 and returning these to the patient in large numbers intravenously in an activated state. Anti-CD3 antibody is commonly used to promote the proliferation of T cells in culture. Cells used in adoptive therapy can be genetically modified using recombinant DNA technology to achieve any number of goals. Such adoptive T-cell therapies involve genetically engineering a subject's or patient's own T cells to produce recombinant receptors on their surface referred to as "chimeric antigen receptors" (CARs). CARs are proteins that allow the T cells to recognize a specific protein (antigen) on tumor cells. These engineered CAR T cells are then expanded in the laboratory until they number in the billions. The expanded population of CART cells is then infused into the patient. After the infusion, the T cells multiply in the subject's body and, with guidance from their engineered receptor, recognize and kill cancer cells that display the antigen on their surfaces.

Examples of dendritic cell (DC) immunotherapies or dendritic cell vaccines include modified dendritic cells and any other antigen presenting cell, autologous or xeno, whether modified by multiple antigens, whole cancer cells, single antigens, by mRNA, phage display or any other modification, including but not restricted to ex vivo-generated, antigen-loaded dendritic cells (DCs) to induce antigen-specific T-cell immunity, ex vivo gene-loaded DCs to induce humoral immunity, ex vivo-generated, antigen-loaded DCs to induce tumor-specific immunity, and ex vivo-generated immature DCs to induce tolerance, including, but not limited to, Provenge and others.

Examples of viral therapies include oncolytic viruses or virus-derived genetic or other material designed to elicit anti-tumor immunity and inhibitors of infectious viruses associated with tumor development, such as drugs in the Prophage series. Examples of monoclonal antibodies include Alemtuzumab, Bevacizumab, Cetuximab, Gemtuzumab ozogamicin, Rituximab, Trastuzumab, Radioimmunotherapy, Ibritumomab tiuxetan, and Tositumomab/iodine tositumomab regimen. An immunotherapy can be used as a monotherapy or used in combination with one or more other therapies (one or more other immunotherapies or non-immunotherapies including, e.g., chemotherapeutic agents).

Enhancing or prolonging T-cell activation using antibody-based immunotherapies such as monoclonal antibodies (mAbs) blocking negative signaling receptors, such as CTLA-4, is an approach to overcoming tumor-induced immune tolerance. Ipilimumab and Tremelimumab inhibit CTLA-4, prolonging antitumor immune responses and leading to durable anti-tumor effects (Graziani G. et al., "Ipilimumab: A Novel Immunostimulatory Monoclonal Antibody for the Treatment of Cancer," Pharmacol. Res., 2012, January, Epub 2011 Sep. 10, 65(1):9-22; and Tarhini A. A. et al., "CTLA-4 Blockade: Therapeutic Potential in Cancer Patients," Onco. Targets Ther., 2010, 3:15-25, which are each incorporated herein by reference in their entirety). Ipilumumab has been approved by the U.S. Food and Drug Administration for the treatment of unresectable or metastatic melanoma.

By enriching for, or otherwise manipulating the proportion of non-classical and intermediate monocytes in the sample used to generate DCs for DC immunotherapies, one can promote patient responsiveness to immunotherapy, thereby increasing or enhancing a patient's or subject's response to a given immunotherapy as measured, for example, by a decrease in unwanted cellular proliferation; reduction in the number of cancer cells; reduction of tumor size; inhibition of (i.e., slow to some extent and preferably stop) cancer cell infiltration into peripheral organs; inhibition of (i.e., slow to some extent and preferably stop) tumor metastasis; inhibition of, to some extent, tumor growth; reduction of signaling in the target cells, and/or relief, to some extent, of one or more of the symptoms associated with the cancer.

An immunotherapy should be administered in a therapeutically effective amount, as that term is defined herein. The amount administered and the exact treatment regimen (dosage, timing, duration of treatment, etc.) will depend on the exact immunotherapeutic administered and the specific indication treated. As such, it is not practical to set out an exact therapeutically effective amount herein. Nonetheless, the ordinary skilled practioner can readily determine and adjust amounts necessary for a specific treatment without undue experimentation. Effective amounts of an immunotherapy can be evaluated, at least in part, using animal models of the disease or disorder in question. It should be noted that a therapeutically effective amount of an immunotherapeutic can initially cause a tumor to enlarge, from lymphocyte infiltration. To the extent the administered agent directly or indirectly prevents growth of and/or kills existing cancer cells, it may be cytostatic and/or cytotoxic. For cancer therapy, efficacy of the immunotherapeutic or other agent can, for example, be measured by assessing the time to disease progression (TTP), survival, and/or determining the response rate (RR).

Dendritic cell therapy and other immunotherapies can promote and/or benefit from co-stimulatory molecules which act to provide a stimulatory signal to a T cell to activate T-cell dependent immune responses. Non-limiting examples of co-stimulatory molecules include CD80, CD83, CD86, MHC Class II (also referred to in humans as HLA, such as HLA-DR), members of the B7-family of co-stimulatory molecules, CD40, CD40 ligand, CD30, CD30 ligand, 4-IBB receptor, 4-IBB ligand, CD27, FAS receptor, FAS ligand, TRAIL receptor, TRAIL ligand. In some embodiments of the various aspects described herein, the one or more co-stimulatory molecules is selected from CD80, CD83, CD86, and MHC Class II or HLA-DR. The measurement or detection of co-stimulatory molecules can be performed using methods known in the art.

Accordingly, one of skill in the art can readily determine if a population of dendritic cells prepared from a population enriched for non-classical and/or intermediate monocytes expresses one or more co-stimulatory molecules at a level greater than that expressed by dendritic cells prepared, for example, by in vitro differentiation of a non-enriched monocyte population, or whether there is increased expression of one or more co-stimulatory molecules relative to a population of dendritic cells derived from $CD14^+CD16^-$ monocytes.

In some embodiments of these aspects and all such aspects described herein, the non-classical monocytes were $CD16^+$ and $CD14^{dim}/CD14^-$ and the intermediate monocytes were $CD16^+$ and $CD14^+$ prior to their differentiation to dendritic cells.

In some embodiments of these aspects and all such aspects described herein, the immunotherapy comprises inhibition of an immune checkpoint or immune checkpoint molecule that normally acts to dampen or inhibit an immune response.

Immune checkpoint molecules that can be targeted, e.g., via antibodies, or, for example, small molecule inhibitors include, but are not limited to, Programmed Death 1 (PD-1, also known as PDCD1 or CD279), Cytotoxic T-Lymphocyte Antigen 4 (CTLA-4), LAG3 (also known as CD223), TIM3 (also known as HAVCR2), BTLA (also known as CD272), BY55 (also known as CD160), TIGIT (also known as VSTM3), B7H5 (also known as C10orf54), LAIR1 (also known as CD305), SIGLEC10, and 2B4 (also known as CD244), which directly inhibit immune cells.

Accordingly, in some embodiments of these aspects and all such aspects described herein, the inhibition of an immune checkpoint comprises inhibition of PD-1, PD-L1, TIM-3, CTLA4, LAG-3 and/or TIGIT, among others.

In some embodiments of these aspects and all such aspects described herein, the inhibition comprises administering an antibody that binds to and inhibits a checkpoint regulator protein.

In some embodiments of these aspects and all such aspects described herein, the sample of monocytes used to prepare an enriched population of monocytes and/or to prepare dendritic cells comprises circulating monocytes.

In some embodiments of these aspects and all such aspects described herein, the sample of monocytes comprises bone marrow monocytes and/or monocyte progenitors. Methods for bone-marrow sampling or harvesting are known to those of skill in the art.

In some embodiments of these aspects and all such aspects described herein, the population of cells enriched for non-classical and intermediate monocytes is prepared by contacting a sample of monocytes or monocyte progenitors with one or more cytokines. In these aspects, the contacting promotes the transition of classical monocytes to an intermediate or non-classical phenotype. Cytokines that promote the transition include, for example, are selected from macrophage colony-stimulating factor, TGF-β1, and MCP-1.

In some embodiments of these aspects and all such aspects described herein, the non-classical and intermediate monocytes treated to generate dendritic cells comprised at least 10% of the population of monocytes treated. In some embodiments of these aspects and all such aspects described herein, the non-classical and intermediate monocytes comprised at least 15% of the population of monocytes.

Whether non-classical and/or intermediate monocytes are enriched directly from circulating monocytes or by treatment of a monocyte population with cytokines that promote the non-classical/intermediate phenotype, the proportion of non-classical and/or intermediate monocytes can be enriched or further enriched through cell sorting, such as, for example, flow cytometric cell sorting, magnetic-bead based cell sorting, or a combination thereof.

Cell sorting includes, for example, immunological-based methods of positive and negative selection, which result in the physical isolation of a cell type, such as a monocyte subset, having a specific cell surface marker or combination of markers using an antibody or an antibody fragment, or a combination of antibodies or antibody fragments, which specifically recognize(s) the marker(s). Examples include, but are not limited to cell sorting by fluorescence-activated cell sorting (FACS), magnetic beads [Magnetic-activated cell sorting (MACS)], column-based cell sorting, and immunopanning.

Positive selection techniques result in the isolation or enrichment of cells expressing specific cell-surface markers, while negative selection techniques result in the isolation or enrichment of cells not expressing specific cell-surface markers. Where necessary or desired, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select cells expressing one or more specific cell-surface markers, such as monocytes. For example, in a negative selection protocol, a biological sample, such as a cell sample, is first contacted with labeled antibodies specific for one or more cell-surface markers of interest, and the sample is then contacted with beads that are specific for the labels of the antibodies, and the cells expressing any of the markers of interest are removed using immunomagnetic lineage depletion.

Magnetic and bead-based sorting methods use antibodies affixed to magnetic beads, biodegradable beads, and/or non-biodegradable beads, or combinations thereof. In such methods, the biological sample, such as circulating blood, is contacted with magnetic beads coated with antibodies against one or more specific cell-surface antigens, such as CD14 and/or CD16. This causes the cells in the sample expressing this antigen to attach to the magnetic beads. Afterwards the contacted cell solution is transferred to a strong magnetic field, such as a column or rack having a magnet. The cells attached to the beads (expressing the cell-surface marker) stay on the column or sample tube, while other cells (not expressing the cell-surface marker) flow through or remain in solution. Using this method, cells can be separated positively or negatively (or both), with respect to the particular cell-surface markers. In some embodiments, magnetic activated cell sorting (MACS) strategies are used with the compositions and methods described herein.

Other embodiments of the aspects described herein use flow cytometric methods, alone or in combination with magnetic bead based methods, to isolate or enrich for monocytes. Flow cytometry provides a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. Increasing the number of lasers and detectors allows for labeling by multiple antibodies, and can more precisely identify a target population by their phenotypic markers. Certain flow cytometric instruments can take digital images of individual cells, allowing for the analysis of fluorescent signal location within or on the surface of cells.

A common variation of flow cytometric techniques is to physically sort particles based on their properties, so as to purify populations of interest via fluorescence-activated cell sorting, which permits sorting a heterogeneous mixture of cells from a single biological sample into one or more containers, one cell at a time, based upon the specific light scattering and fluorescent characteristics of each cell. This provides fast, objective and quantitative recording of fluorescent signals from individual cells as well as physical separation of cells of particular interest. Accordingly, in those embodiments when the agents specific for cell-surface markers are antibodies labeled with tags that can be detected by a flow cytometer, fluorescence-activated cell sorting (FACS) can be used in and with the methods described herein to isolate and enrich for populations of non-classical and/or intermediate monocytes.

In some embodiments of these aspects and all such aspects described herein, a sample of monocytes is isolated from a cancer patient.

The compositions and methods described herein provide, in part, novel means of preparing enhanced monocyte subsets useful for the generation of dendritic cells with enhanced efficacy for use in DC vaccines for the treatment of cancer or a tumor. A "tumor" as used herein refers to an uncontrolled growth of cells which can interfere with the normal functioning of the bodily organs and systems. A "cancer" is an uncontrolled growth or proliferation of cells that has gained the ability for at least some of its cells to leave the primary site of growth amd seed other tissues or organs, i.e., the ability to metastasize, as the term is used herein. A patient subject that has a cancer or a tumor, i.e., a cancer or tumor patient, is a subject having objectively measurable cancer (metastasized) or tumor cells present in the subject's body. Included in the definition of a tumor are benign and malignant tumors, as well as dormant tumors or micrometastases. Cancers which migrate from their original location and seed vital organs can eventually lead to the death of the subject through the functional deterioration of the affected organs. Hematopoietic cancers, such as leukemia, are able to out-compete the normal hemopoietic compartments in a subject, thereby leading to hemopoietic failure (in the form of anemia, thrombocytopenia and neutropenia) ultimately causing death.

Metastasis is the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the cancer cell regulate this behavior, and interactions between the cancer cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer that can be treated using the methods and compositions described herein include, but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), tumors of primitive origins and Meigs' syndrome.

Also provided herein, in some aspects, are methods to increase efficacy of an immunotherapy comprising: contacting a sample comprising monocytes with one or more cytokines that promote the transition of monocytes in the sample to a non-classical and/or intermediate phenotype, and maturing the monocytes under conditions that permit the transition. The matured monocytes are enriched for non-classical and intermediate monocytes as described herein relative to the starting sample of monocytes. The enriched population permits enhanced efficacy of an immunotherapy when differentiated to dendritic cells.

In some aspects, provided herein are methods to increase efficacy of an immunotherapy comprising a first step (a) of contacting a sample comprising monocytes or monocyte progenitors with one or more cytokines that promote the transition of monocytes in the sample to a non-classical or intermediate phenotype and maturing the monocytes under conditions that permit such differentiation. The matured monocytes are thus enriched for non-classical and intermediate monocytes derived from the sample of monocytes (the population of non-classical monocytes is $CD16^+$ and $CD14^{dim}/CD14^-$ and the population of intermediate monocytes is $CD16^+$ and $CD14^+$). The second step (b) involves culturing the resulting enriched non-classical and intermediate monocytes in a dendritic cell maturation cocktail to generate dendritic cells with enhanced efficacy in an immunotherapy.

In addition, in some aspects, provided herein are assays comprising: (a) contacting a sample comprising monocytes obtained from a subject with an agent specific for CD16 and an agent specific for CD14; and (b) analyzing expression of CD16 and CD14 on the monocytes of the contacted sample, such that if a population of $CD16^+$ and $CD^{dim}/CD14^-$ and/or $CD16^+$ and $CD14^+$ cells comprises at least 10% of the monocytes in the sample, then the subject is determined or predicted to have increased responsiveness to dendritic cell therapy; and if a population of $CD16^+$ and $CD14^{dim}/CD14^-$ and/or $CD16^+$ and $CD14^+$ cells comprises less than 10% of the monocytes in the sample, then the subject is determined or predicted to have decreased responsiveness to dendritic cell therapy, unless steps are taken to modify the proportions of $CD16^+$, $CD14^{dim}/CD14^-$ and/or $CD16^+$, $CD14^+$ cells.

Also provided herein, in some aspects, are methods of determining or predicting the responsiveness of a subject to a dendritic cell therapy comprising: (a) contacting a sample comprising monocytes obtained from a subject with an agent specific for CD16 and an agent specific for CD14; and (b) analyzing expression of CD16 and CD14 on the monocytes of the contacted sample, wherein if a population of CD16$^+$ and CD14$^{dim}$/CD14$^-$ and/or CD16$^+$ and CD14$^+$ cells comprises at least 10% of the monocytes in the sample, then the subject is determined or predicted to have increased responsiveness to dendritic cell therapy; and wherein if a population of CD16$^+$ and CD14$^{dim}$/CD14$^-$ and/or CD16$^+$ and CD14$^+$ cells comprises less than 10% of the monocytes in the sample, then the subject is determined or predicted to have decreased responsiveness to dendritic cell therapy.

In some embodiments of these aspects and all such aspects described herein, the sample of monocytes comprises circulating monocytes or bone marrow monocytes or monocyte progenitors.

In some embodiments of the assays and methods described herein, the sample comprising monocytes is isolated from a cancer patient.

The assays and methods described herein comprise, in part, agents that specifically bind the cell-surface markers CD14 or CD16, to identify the various monocyte subset populations in a sample comprising monocytes. The assays and methods described herein involve, in part, analysis of the expression of CD14 and CD16 and determination of whether a cell or population of cells has positive/high, dim/low, or negative expression of CD14 and CD16. A cell can be designated "positive" or "high," "dim" or "low," or "negative" for any of the cell-surface markers described herein, and all such designations are useful for the practice of the assays and methods described herein. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell may express messenger RNA for a cell-surface marker, in order to be considered positive for the assays and methods described herein, the cell must express the cell surface marker of interest on its surface. A cell is considered "dim" or "low" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell, but there exists another distinct population of cells that expresses the marker at a higher level, giving rise to at least two populations that are distinguishable when analyzed using, for example, flow cytometry. Similarly, a cell is considered "negative" for a cell-surface marker if it does not express the marker on its surface in amounts sufficient to be detected using methods known to those of skill in the art, such as contacting a cell with an antibody that binds specifically to that marker and subsequently performing flow cytometric analysis of such a contacted cell to determine whether the antibody is bound the cell.

As used herein, an "agent specific for" a particular cell-surface biomarker, such as CD14 or CD16, refers to an agent that can selectively react with or bind to that cell-surface marker, but has little or no detectable reactivity to other cell-surface markers or antigens. For example, an agent specific for CD14 will not react with or bind to CD16, and vice versa. Thus, agents specific for cell-surface markers recognize unique structural features of the markers. In some embodiments, an agent specific for a given cell-surface marker binds to the cell-surface marker, but does not cause initiation of downstream signaling events mediated by that cell-surface marker, for example, a non-activating antibody. Agents specific for cell-surface molecules include, but are not limited to, antibodies or antigen-binding fragments thereof, natural or recombinant ligands, small molecules; nucleic acid molecules and nucleic acid analogues; intrabodies; aptamers; and other proteins or peptides. In some embodiments of the assays and methods described herein, the agents specific for CD14 and/or the agents specific for CD16 are antibodies or antigen-binding fragments thereof. In some embodiments of the assays and methods described herein, the antibodies or antigen-binding fragments thereof specific for CD14, and/or the antibodies or antigen-binding fragments thereof specific for CD16, are labeled.

In some embodiments of this aspect and all aspects described herein, the preferred agents specific for the cell-surface markers CD14 and/or CD16 are antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding antibody fragment. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)]. Such antibodies or antigen-binding fragments specific for CD14 and CD16 are available commercially from vendors such as R&D Systems, BD Biosciences, e-Biosciences and Miltenyi, or can be raised against these cell-surface markers by methods known to those skilled in the art.

In some embodiments of the aspects described herein, the agents specific for the cell-surface markers CD14 and/or CD16, such as an antibody or antigen-binding fragment, are labeled or tagged to facilitate the detection and/or isolation of the monocyte subsets.

Labeled or tagged antibodies include antibodies that are labeled by detectable means and include, but are not limited to, antibodies that are fluorescently, enzymatically, radioactively, and/or chemiluminescently labeled. Antibodies can also be labeled with a detectable peptide tag, such as c-Myc, HA, VSV-G, HSV, FLAG, V5, or HIS tags, which can be detected using an antibody specific to the tag, for example, an anti-c-Myc antibody. Various methods of labeling polypeptides and glycoproteins are known in the art and can be used to prepare reagents as needed for the methods and assays described herein. Non-limiting examples of fluorescent labels or tags for labeling the antibodies for use in the assays and methods described herein include Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

The assays and methods described herein involve, in part, analysis of expression of CD16 and CD14 on the monocytes of the contacted sample. Preferably, such analysis is performed using flow cytometric analysis, which is known in the art ad discussed herein above.

The analysis of monocyte subsets using the assays and methods described herein is used, in some aspects and embodiments, to predict, identify, or determine which patients will have increased responsiveness to immunotherapy, e.g., increased responsiveness to dendritic cell therapy. In some such embodiments, the assays and methods further comprise administering or modifying a treatment step based upon the predicted responsiveness.

In some embodiments of the assays and methods described herein herein, if the population of CD16$^+$ and CD14$^{dim}$/CD14$^-$ and/or CD16$^+$ and CD14$^+$ cells comprises less than 10% of the monocytes in the sample, the assay or method further comprises contacting a sample from the subject comprising monocytes with one or more cytokines that promote the transition of monocytes in the sample to a non-classical or intermediate phenotype, and maturing the monocytes under conditions that permit the transition. Such methods and assays also involve, e.g., differentiation of those monocytes ex vivo or in vitro to dendritic cells, contacting such dendritic cells with tumor antigen, for example, and administering the contacted dendritic cells to the subject. Alternatively, in some embodiments, the subject predicted to have decreased responsiveness to dendritic cell therapy can be administered an agent, e.g., a cytokine, that promotes or increases transition of monocytes to an intermediate or non-classical phenotype prior to treatment of monocytes from such subject in vitro to promote dendritic cell differentiation for use as a dendritic cell vaccine. In some such embodiments, the methods or assays further comprise enriching for non-classical and intermediate monocytes from the sample of monocytes, wherein the population of non-classical monocytes is CD16$^+$ and CD14$^{dim}$/CD14$^-$ and the population of intermediate monocytes is CD16$^+$ and CD14$^+$.

In some embodiments of these aspects and all such aspects described herein, the enriching comprises or further comprises cell sorting.

In some embodiments of these aspects and all such aspects described herein, the cell sorting comprises flow cytometric cell sorting, magnetic-bead based cell sorting, or a combination thereof.

In some embodiments of the assays and methods described herein comprising enriching for non-classical and intermediate monocytes from a sample of monocytes, the dendritic cells derived from the enriched non-classical and intermediate monocytes have increased expression of one or more co-stimulatory molecules relative to a population of dendritic cells derived from CD14$^+$CD16$^-$ monocytes.

In some embodiments of these assays and methods, the one or more co-stimulatory molecules is selected from CD80, CD83, CD86, and MHC Class II or HLA-DR.

In some embodiments of these assays and methods described herein which further comprise contacting a sample from the subject comprising monocytes with one or more cytokines that promote the transition of monocytes in the sample to a non-classical or intermediate phenotype, the one or more cytokines comprises macrophage colony-stimulating factor, TGF-β1, and MCP-1.

In some embodiments, the assays and methods described herein further comprise culturing the enriched non-classical and intermediate monocytes in a dendritic cell maturation cocktail.

In some embodiments, an isolated cell or cell population, such as a population of monocytes, is further cultured in vitro or ex vivo, e.g., in the presence of growth factors or cytokines, to further expand the number of cells in the isolated cell population or substantially pure cell population or to promote differentiation to a particular cell or cell subtype(s), such as non-classical and/or intermediate monocytes. Such culture can be performed using any method known to one of skill in the art, for example, as described in the Examples section.

Also provided herein, in some aspects, are methods of treatment of a subject having cancer, the method comprising administering to the subject a dendritic cell vaccine comprising dendritic cells prepared from the compositions described herein or dendritic cells prepared using any of the methods described herein.

The compositions and methods described herein provide novel means of preparing enhanced monocyte subsets useful for the generation of dendritic cells with enhanced efficacy for use in DC vaccines for the treatment of cancer, which includes alleviating one or more symptoms of a cancer or a tumor. As used herein, the phrase "alleviating a symptom of a cancer or tumor" is ameliorating any condition or symptom associated with the cancer such as the symptoms of the cancer being treated, the presence or size of metastases or micrometastases, the size of the primary tumor, the presence or the size of the dormant tumor, etc. As compared with an equivalent untreated control, such as a subject prior to the use of the compositions and methods described herein, such reduction or degree of prevention is at least 5%, at least 10%, at least 20%, at least 40%, at least 50%, at least 60%, at least 80%, at least 90%, at least 95%, or more as measured by any standard technique known to one of ordinary skill in the art. A patient or subject who is being treated for a cancer or tumor is one who a medical practitioner has diagnosed as having such a condition. Diagnosis can be by any suitable means.

In regard to any of the compositions, methods, and uses described herein, the object of therapeutic treatments is to reverse, alleviate, ameliorate, inhibit, slow down or stop the progression or severity of a condition associated with, a disease or disorder. Treatments include reducing or alleviating at least one adverse effect or symptom of a disease or disorder. Treatment is generally effective if one or more symptoms or clinical markers are reduced, or if the progression of a disease is reduced or halted. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. Treating a disease also includes providing relief from the symptoms or side-effects of the disease (including palliative treatment).

Effective amounts, toxicity, and therapeutic efficacy can be determined by standard pharmaceutical procedures in experimental animals. A therapeutically effective dose can be estimated initially using, for example, animal cancer models.

In some embodiments of the compositions and methods described herein, a tumor or cancer antigen can also be administered to a subject or patient being administered dendritic cells derived from non-classical and/or intermediate monocytes, as described herein.

A number of tumor antigens have been identified that are associated with specific cancers. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can b0e characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. For example, viral proteins such as hepatitis B (HBV), Epstein-Barr (EBV), and human papilloma (HPV) have been shown to be important in the development of hepatocellular carcinoma, lymphoma, and cervical cancer, respectively. However, tumors use or benefit from a range of different immune evasion mechanisms, such that the immune systems of cancer patients often fail to respond to the tumor antigens. Some examples of cancer antigens that are normally associated with spermatocytes or spermatogonia of the testis, placenta, and ovary include the cancer-testis (CT) antigens BAGE, GAGE, MAGE-1 and MAGE-3, NY-ESO-1, SSX. These antigens are found in melanoma, lymphoma, lung, bladder, colon, and breast carcinomas (e.g., as described in Butterfield et al., J. Immunotherapy 2008; 31:294-309; Markowicz et al., J Clin Oncol 27:15s, 2009 (suppl; abstr 9039)). Cancer antigens normally found in melanocytes, epithelial tissues, prostate, and colon also include the differentiation antigens Gp100, Melan-A/Mart-1, Tyrosinase, PSA, CEA, and Mammaglobin-A. These antigens are found in melanoma, prostate cancer, and in colon and breast carcinomas. Some cancer antigens are shared antigens that are ubiquitously expressed at low levels but overespressed in cancers. Examples of overexpressed cancer antigens include p53, HER-2/neu, livin, and survivin, found in esophagus, liver, pancreas, colon, breast, ovary, bladder, and prostate carcinomas. Other cancer antigens are unique, such as β-catenin-m, β-Actin/4/m, Myosin/m, HSP70-2/m, and HLA-A2-R170J, which are associated with one or more of melanoma, non-small cell lung cancer, and renal cancer. Still other cancer antigens are the tumor-associated carbohydrate antigens that are normally found in epithelia tissues such as renal, intestinal, and colorectal tissues. These cancer antigens include GM2, GD2, GD3, MUC-1, sTn, abd globo-H, which can be found in melanoma, neuroblastoma, colorectal, lung, breast, ovarian, and prostate cancers. Additional tumor antigens, peptide epitopes, and descriptions thereof are described in U.S. Pat. Nos. 7,906,620; 7,910,692; 8,097, 242; 7,935,531; 8,012,468; 8,097,256; 8,003,773; Tartour et al., Immunol Lett 2000; 74(1): 1-3, the contents of which are herein incorporated by reference in their entireties. In some embodiments, the intact cancer antigen is used, whereas in other embodiments, a peptide epitope of the cancer antigen (prepared either by proteolytic digestion or recombinantly) is used.

In some embodiments of the compositions and methods described herein, an anti-cancer therapy or agent can also be administered to a subject or patient being administered dendritic cells derived from non-classical and/or intermediate monocytes, as described herein.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets PD1, PDL1, PDL2, TIM3 or any TIM family member, CEACAM1 or any CEACAM family member, ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also specifically contemplated for the methods described herein.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including active fragments and/or variants thereof.

In some embodiments of the compositions and methods described herein, a chemotherapeutic agent can also be administered to a subject or patient being administered dendritic cells derived from non-classical and/or intermediate monocytes, as described herein.

Non-limiting examples of chemotherapeutic agents can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB.); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. In addition, the methods of treatment can further include the use of radiation or radiation therapy.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; Baltzer L, Berkery R (eds): Oncology Pocket Guide to Chemotherapy, 2nd ed. St. Louis, Mosby-Year Book, 1995; Fischer D S (ed): The Cancer Chemotherapy Handbook, 4th ed. St. Louis, Mosby-Year Book, 2003).

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

Compositions comprising dendritic cells generated using the compositions and methods described herein can be administered to a subject in need thereof by any appropriate route which results in an effective treatment in the subject. Administration of a dendritic cell vaccine will most often be intravenous. Other agents administered either simultaneously or sequentially can be administered by routes known to those of ordinary skill in the art. As used herein, the terms "administering," and "introducing" are used interchangeably and refer to the placement of dendritic cells generated using the compositions and methods described herein into a subject by a method or route which eventually results in partial localization of such cells at a desired site, such as a tumor site, such that a desired effect(s) is produced.

A variety of means for administering cells to subjects are known to those of skill in the art. Such methods can include systemic injection, for example i.v. injection, or implantation of cells into a target site in a subject. Cells can be inserted into a delivery device which facilitates introduction by injection or implantation into the subject. Such delivery devices can include tubes, e.g., catheters, for injecting cells and fluids into the body of a recipient subject. In some embodiments, the tubes additionally have a needle, e.g., through which the cells can be introduced into the subject at a desired location. The cells can be prepared for delivery in a variety of different forms. For example, the cells can be suspended in a solution or gel or embedded in a support matrix when contained in such a delivery device. Cells can be mixed with a pharmaceutically acceptable carrier or diluent in which the cells remain viable.

Pharmaceutically acceptable carriers and diluents include saline, aqueous buffer solutions, solvents and/or dispersion media. The use of such carriers and diluents is known in the art. The solution is preferably sterile and fluid. Preferably, prior to the introduction of cells as described herein, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Direct injection techniques for cell administration can also be used to stimulate transmigration of cells through the entire vasculature, or to the vasculature of a particular organ, such as for example liver, or kidney or any other organ. This includes non-specific targeting of the vasculature. One can target any organ by selecting a specific injection site, e.g., a liver portal vein. Alternatively, the injection can be performed systemically into any vein in the body. If so desired, a mammal or subject can be pre-treated with an agent, for example an agent administered to enhance cell targeting to a tissue (e.g., a homing factor) can be placed at that site to encourage cells to target the desired tissue. For example, direct injection of homing factors into a tissue can be performed prior to systemic delivery of cells.

In some embodiments of these aspects and all such aspects described herein, dendritic cells derived from the non-classical and intermediate monocytes have increased expression of one or more co-stimulatory molecules relative to a population of $CD14^+CD16^-$ monocytes.

In some embodiments of these aspects and all such aspects described herein, the one or more co-stimulatory molecules is selected from CD80, CD83, CD86, and MHC Class II or HLA-DR.

In some embodiments of these aspects and all such aspects described herein, the one or more cytokines that promote(s) monocyte transition from a classical to an intermediate or non-classical phenotype comprises macrophage colony-stimulating factor, TGF-β1, and MCP-1.

In some embodiments of these aspects and all such aspects described herein, the methods of preparing dendritic cells with enhanced efficacy as dendritic cell vaccines further comprises cell sorting or enrichment by cell sorting.

In some embodiments of these aspects and all such aspects described herein, the cell sorting comprises flow cytometric cell sorting, magnetic-bead based cell sorting, or a combination thereof.

In some embodiments of these aspects and all such aspects described herein, the sample of monocytes used to generate a population enriched for intermediate or non-classical phenotype monocytes is isolated from a cancer patient.

In some embodiments of these aspects and all such aspects described herein, the sample of monocytes comprises circulating monocytes.

In some embodiments of these aspects and all such aspects described herein, the sample of monocytes comprises bone marrow monocytes or monocyte progenitors.

In some embodiments of these aspects and all such aspects described herein, the method further comprises culturing the enriched for non-classical and intermediate monocytes in a dendritic cell maturation cocktail.

In some embodiments of these aspects and all such aspects described herein, the immunotherapy comprises a dendritic cell vaccine.

Specifically contemplated herein, in some aspects, are methods promoting patient responsiveness to immunotherapy, the method comprising administering an agent that promotes the transition of classical monocytes to intermediate or non-classical monocyte phenotypes.

In some embodiments of these aspects and all such aspects described herein, the agent comprises one or more cytokines.

In some embodiments of these aspects and all such aspects described herein, the cytokine is/are selected from the group consisting of mCSF, TGF-β1, MCP-1.

In some embodiments of these aspects and all such aspects described herein, the immunotherapy comprises a cell-based, cytokine-based or antibody-based therapy.

In some embodiments of these aspects and all such aspects described herein, the cell-based immunotherapy comprises dendritic cell vaccination and/or adoptive T cell therapy.

In some embodiments of these aspects and all such aspects described herein, the immunotherapy comprises inhibition of an immune checkpoint.

In some embodiments of these aspects and all such aspects described herein, the inhibition of an immune checkpoint comprises inhibition of PD-1, PD-L1, TIM-3, CTLA4, LAG-3 and/or TIGIT. In some embodiments of these aspects and all such aspects described herein, the inhibition comprises administering an antibody that binds to and inhibits a checkpoint regulator protein.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A composition for preparing dendritic cells for immunotherapy, the composition comprising:
   a. a sample of monocytes or monocyte progenitors in admixture with a cytokine preparation comprising one or more cytokines selected from the group consisting of macrophage colony-stimulating factor, TGF-β1, and MCP-1; and
   b. a tissue culture medium.
2. The composition of paragraph 1, wherein said sample of monocytes comprises circulating monocytes.
3. The composition of paragraph 1, wherein said sample of monocytes or monocyte progenitors comprises bone marrow monocytes or monocyte progenitors.
4. The composition of paragraph 1, wherein incubation of said composition results in a population of monocytes enriched for non-classical and/or intermediate monocytes which, when differentiated to dendritic cells in vitro, provides dendritic cells with greater efficacy in a dendritic cell vaccine than dendritic cells produced from a non-enriched population of monocytes.
5. A preparation of monocytes comprising at least 10% non-classical and/or intermediate monocytes, in admixture with one or more cytokines selected from the group consisting of macrophage colony-stimulating factor, TGF-β1, and MCP-1.
6. The preparation of paragraph 5, further comprising a tissue culture medium.
7. The preparation of paragraph 5, which comprises at least 15% non-classical and/or intermediate monocytes.
8. A pharmaceutical composition for promoting patient responsiveness to immunotherapy, the composition comprising:
   a. a population of dendritic cells prepared by in vitro differentiation of a population of monocytes enriched for non-classical and/or intermediate monocytes relative to the proportions of non-classical and/or intermediate monocytes occurring in vivo, wherein said dendritic cells express one or more co-stimulatory molecules at a level greater than that expressed by dendritic cells prepared by in vitro differentiation of a non-enriched monocyte population; and
   b. a pharmaceutically acceptable excipient, diluent, and/or carrier.
9. The composition of paragraph 8, wherein the non-classical monocytes were $CD16^+$ and $CD14^{dim}/CD14^-$ and the intermediate monocytes were $CD16^+$ and $CD14^+$ prior to their differentiation to dendritic cells.
10. The composition of paragraph 1 or paragraph 8, wherein said immunotherapy comprises a cell-based, cytokine-based and/or antibody-based therapy.
11. The composition of paragraph 10, wherein said cell-based immunotherapy comprises dendritic cell vaccination and/or adoptive T cell therapy.
12. The composition of paragraph 1 or paragraph 8, wherein said immunotherapy comprises inhibition of an immune checkpoint.
13. The composition of paragraph 12, wherein said inhibition of an immune checkpoint comprises inhibition of PD-1, PD-L1, TIM-3, CTLA4, LAG-3 and/or TIGIT.
14. The composition of paragraph 12, wherein said inhibition comprises administering an antibody that binds to and inhibits a checkpoint regulator protein.
15. The composition of paragraph 5 or paragraph 8, wherein said sample of monocytes comprises circulating monocytes.
16. The composition of paragraph 5 or paragraph 8, wherein said sample of monocytes comprises bone marrow monocytes and/or monocyte progenitors.
17. The composition of paragraph 8, wherein the one or more co-stimulatory molecules is selected from CD80, CD83, CD86, and MHC Class II.
18. The composition of paragraph 8, wherein the population of cells enriched for non-classical and/or intermediate monocytes is prepared by contacting a sample of monocytes or monocyte progenitors with one or more cytokines.
19. The composition of paragraph 18, wherein said contacting promotes the transition of classical monocytes to an intermediate or non-classical phenotype.
20. The composition of paragraph 18, wherein the one or more cytokines are selected from macrophage colony-stimulating factor, TGF-β1, and MCP-1.
21. The composition of any one of paragraphs 8-20, wherein the population of cells enriched for non-classical and/or intermediate monocytes is prepared by a method comprising cell sorting.
22. The composition of paragraph 21, wherein the cell sorting comprises flow cytometric cell sorting, magnetic-bead based cell sorting, or a combination thereof.
23. The composition of paragraph 1 or paragraph 8, wherein the sample of monocytes is isolated from a cancer patient.
24. The composition of paragraph 8, wherein the non-classical and/or intermediate monocytes comprised at least 10% of the population of monocytes.
25. The composition of paragraph 8, wherein the non-classical and/or intermediate monocytes comprised at least 15% of the population of monocytes.
26. A pharmaceutical composition comprising:
   a. a population of dendritic cells prepared by in vitro differentiation of a population of monocytes enriched for non-classical and/or intermediate monocytes relative to the proportions of non-classical and/or intermediate monocytes occurring in vivo, wherein said dendritic cells express one or more co-stimulatory molecules at a level greater than that expressed by dendritic cells prepared by in vitro differentiation of a non-enriched monocyte population; and
   b. a pharmaceutically acceptable excipient, diluent, and/or carrier.
27. The pharmaceutical composition of paragraph 26, wherein said sample of monocytes comprises circulating monocytes.
28. The pharmaceutical composition of paragraph 26, wherein said sample of monocytes comprises bone marrow monocytes and/or monocyte progenitors.
29. The pharmaceutical composition of paragraph 26, wherein dendritic cells derived from said non-classical and/or intermediate monocytes exhibit increased expression of one or more co-stimulatory molecules relative to a dendritic cell population derived from $CD14^+CD16^-$ monocytes.
30. The pharmaceutical composition of paragraph 26, wherein the one or more cytokines are selected from macrophage colony-stimulating factor, TGF-β1, and MCP-1.

31. The pharmaceutical composition of paragraph 26, wherein the one or more co-stimulatory molecules is selected from CD80, CD83, CD86, and MHC Class II.
32. The pharmaceutical composition of paragraph 26, wherein the population of cells enriched for non-classical and/or intermediate monocytes is prepared by a method comprising cell sorting.
33. The pharmaceutical composition of paragraph 32, wherein the cell sorting comprises flow cytometric cell sorting, magnetic-bead based cell sorting, or a combination thereof.
34. The pharmaceutical composition of paragraph 26, wherein the sample of monocytes is isolated from a cancer patient.
35. The pharmaceutical composition of paragraph 26, wherein the non-classical and/or intermediate monocytes comprise at least 10% of the population of cells.
36. The pharmaceutical composition of paragraph 26, wherein the non-classical and/or intermediate monocytes comprise at least 15% of the population of cells.
37. A method to increase efficacy of an immunotherapy comprising:
contacting a sample comprising monocytes with one or more cytokines that promote the transition of monocytes in said sample to a non-classical and/or intermediate phenotype and maturing said monocytes under conditions that permit said transition;
wherein said matured monocytes are enriched for non-classical and/or intermediate monocytes relative to said sample of monocytes, wherein the population of non-classical monocytes is $CD16^+$ and $CD14^{dim}/CD14^-$ and the population of intermediate monocytes is $CD16^+$ and $CD14^+$; and
wherein said enriched population permits enhanced efficacy of an immunotherapy when differentiated to dendritic cells.
38. The method of paragraph 37, wherein dendritic cells derived from the non-classical and/or intermediate monocytes have increased expression of one or more co-stimulatory molecules relative to a population of $CD14^+CD16^-$ monocytes.
39. The method of paragraph 38, wherein the one or more co-stimulatory molecules is selected from CD80, CD83, CD86, and MHC Class II.
40. The method of paragraph 37, wherein the one or more cytokines comprises macrophage colony-stimulating factor, TGF-β1, and MCP-1.
41. The method of paragraph 37, wherein said method further comprises cell sorting.
42. The method of paragraph 41, wherein the cell sorting comprises flow cytometric cell sorting, magnetic-bead based cell sorting, or a combination thereof.
43. The method of paragraph 37, wherein the sample of monocytes is isolated from a cancer patient.
44. The method of paragraph 37, wherein said sample of monocytes comprises circulating monocytes.
45. The method of paragraph 37, wherein said sample of monocytes comprises bone marrow monocytes or monocyte progenitors.
46. The method of paragraph 37, further comprising culturing the enriched for non-classical and/or intermediate monocytes in a dendritic cell maturation cocktail.
47. The method of paragraph 37, wherein said immunotherapy comprises a dendritic cell vaccine.
48. A method to increase efficacy of an immunotherapy comprising:
a) contacting a sample comprising monocytes or monocyte progenitors with one or more cytokines that promote the transition of monocytes in said sample to a non-classical and/or intermediate phenotype and maturing said monocytes under conditions that permit said differentiation;
wherein said matured monocytes are enriched for non-classical and/or intermediate monocytes derived from the sample of monocytes, wherein the population of non-classical monocytes is $CD16^+$ and $CD14^{dim}/CD14^-$ and the population of intermediate monocytes is $CD16^+$ and $CD14^+$; and
b) culturing the enriched for non-classical and/or intermediate monocytes in a dendritic cell maturation cocktail to generate dendritic cells with enhanced efficacy in an immunotherapy.
49. The method of paragraph 48, wherein dendritic cells derived from said non-classical and/or intermediate monocytes have increased expression of one or more co-stimulatory molecules relative to a population of $CD14^+CD16^-$ monocytes.
50. The method of paragraph 49, wherein the one or more co-stimulatory molecules is selected from CD80, CD83, CD86, and MHC Class II.
51. The method of paragraph 48, wherein the one or more cytokines comprises macrophage colony-stimulating factor, TGF-β1, and MCP-1.
52. The method of paragraph 48, further comprising enrichment by cell sorting.
53. The method of paragraph 52, wherein the cell sorting comprises flow cytometric cell sorting, magnetic-bead based cell sorting, or a combination thereof.
54. The method of paragraph 48, wherein the sample of monocytes comprises circulating monocytes or bone-marrow monocytes or monocyte progenitors.
55. The method of paragraph 48, wherein the sample of monocytes is from a cancer patient.
56. The method of paragraph 48, wherein said immunotherapy comprises a dendritic cell vaccine.
57. A method of treatment of a subject having cancer, the method comprising administering to the subject a dendritic cell vaccine comprising dendritic cells prepared from the compositions of any one of paragraphs 1-36 or dendritic cells prepared using the methods of any one of paragraphs 37-56.
58. A method of promoting patient responsiveness to immunotherapy, the method comprising administering an agent that promotes the transition of classical monocytes to intermediate and/or non-classical monocyte phenotypes.
59. The method of paragraph 58, wherein said agent comprises one or more cytokines.
60. The method of paragraph 59, wherein said cytokine(s) is/are selected from the group consisting of mCSF, TGF-β1, and MCP-1.
61. The method of paragraph 58, wherein said immunotherapy comprises a cell-based, cytokine-based or antibody-based therapy.
62. The method of paragraph 61, wherein said cell-based immunotherapy comprises dendritic cell vaccination and/or adoptive T cell therapy.
63. The method of paragraph 58, wherein said immunotherapy comprises inhibition of an immune checkpoint.
64. The method of paragraph 63, wherein said inhibition of an immune checkpoint comprises inhibition of PD-1, PD-L1, TIM-3, CTLA4, LAG-3 and/or TIGIT.

65. The method of paragraph 63, wherein said inhibition comprises administering an antibody that binds to and inhibits a checkpoint regulator protein.
66. A method of identifying a subject with increased responsiveness to dendritic cell therapy comprising:
   a. contacting a sample comprising monocytes obtained from a subject with an agent specific for CD16 and an agent specific for CD14; and
   b. analyzing expression of CD16 and CD14 on the monocytes of the contacted sample,
      wherein if a population of $CD16^+$ and $CD14^{dim}$/$CD14^-$ and/or $CD16^+$ and $CD14^+$ cells comprises at least 10% of the monocytes in the sample, then the subject is determined to have increased responsiveness to dendritic cell therapy; and
      wherein if a population of $CD16^+$ and $CD14^{dim}$/$CD14^-$ and/or $CD16^+$ and $CD14^+$ cells comprises less than 10% of the monocytes in the sample, then the subject is determined to have decreased responsiveness to dendritic cell therapy.
67. The method of paragraph 66, further comprising, when the subject is determined to have increased responsiveness to dendritic cell therapy, the step of administering a dendritic cell vaccine to said subject.
68. The method of paragraph 67, wherein the step of administering a dendritic cell vaccine comprises:
   a) contacting a population of monocytes from said subject with one or more cytokines that promote(s) the differentiation of said monocytes to cells having a dendritic cell phenotype; and
   b) contacting the cells having a dendritic cell phenotype with a tumor antigen and administering the cells with a dendritic cell phenotype to said subject.
69. The method of paragraph 66, wherein if the population of $CD16^+$ and $CD14^{dim}$/$CD14^-$ and/or $CD16^+$ and $CD14^+$ cells comprises less than 10% of the monocytes in the sample, the method further comprises:
   contacting a sample from the subject comprising monocytes with one or more cytokines that promote the transition of monocytes in said sample to a non-classical and/or intermediate phenotype and culturing said monocytes under conditions that permit said transition, such that the monocyte population is enriched for non-classical $CD16^+$ and $CD14^{dim}$/$CD14^-$ monocytes and/or intermediate $CD16^+$ and $CD14^+$ monocytes.
70. The method of paragraph 69, further comprising contacting the enriched population of monocytes with one or more cytokines that promote the differentiation of said monocytes to a dendritic cell phenotype.
71. The method of paragraph 70, further comprising contacting the cells with a dendritic cell phenotype with a tumor antigen and administering the cells with a dendritic cell phenotype to said subject.
72. The method of any one of paragraphs 66-71, wherein said sample of monocytes comprises circulating monocytes or bone marrow monocytes or monocyte progenitors.
73. The method of any one of paragraphs 66-71, wherein dendritic cells derived from the non-classical and/or intermediate monocytes have increased expression of one or more co-stimulatory molecules relative to dendritic cells derived from a population of $CD14^+CD16^-$ monocytes.
74. The method of paragraph 73, wherein the one or more co-stimulatory molecules is selected from CD80, CD83, CD86, and MHC Class II.
75. The method of any one of paragraphs 69-74, wherein the one or more cytokines that promotes the transition of classical monocytes to an intermediate and/or non-classical phenotype comprises macrophage colony-stimulating factor, TGF-β1, and MCP-1.
76. The method of any one of paragraphs 69-75, wherein monocytes are further enriched for monocytes having intermediate and/or non-classical monocyte phenotypes by cell sorting.
77. The method of paragraph 76, wherein the cell sorting comprises flow cytometric cell sorting, magnetic-bead based cell sorting, or a combination thereof.
78. The method of any one of paragraphs 66-78, wherein the sample comprising monocytes is isolated from a cancer patient.

EXAMPLES

Determining which patients are most likely to respond to immunotherapy has been a difficult challenge in the treatment of malignant disease. As demonstrated herein, flow cytometric analysis of circulating monocyte populations for CD16 and CD14 expression provides novel biomarkers for methods and assays to predetermine which patients respond to therapy. As shown herein, prior to dendritic cell vaccination, intermediate ($CD14^+CD16^+$), and non-classical ($CD14^{dim}CD16^+$) monocytes are increased more than two-fold in patients who later had complete responses to dendritic cell therapy. Accordingly, the methods and assays described herein provide, in part, simple blood-based tests for identifying cancer patients that are capable of having complete and durable responses to dendritic cell vaccination.

Described herein are data that show that cancer patient responsiveness to dendritic cell vaccination is influenced by the proportion of intermediate and non-classical phenotype monocytes in a patient's system. These data demonstrate that the monocyte subset composition directly influences the quality of cellular vaccines derived from monocytes. This discovery is applied to dendritic cell therapy or dendritic cell vaccine use by providing patient-derived populations of monocytes enriched for intermediate and non-classical monocytes to be used for differentiating to dendritic cells for dendritic cell vaccination. This has direct impact for commercially available and clinically applied cellular vaccines, such as Sipuleucel-T and AGS-003.

A critical barrier to successful cancer treatment is the inability to initiate durable, tumor-specific responses with conventional therapy such as chemotherapy or radiation. Compared to traditional therapies, immune-based strategies can generate long-lasting systemic protection. Immunotherapy has a role for all cancer types. Dendritic cell vaccination is an immunotherapy designed to induce cancer-specific T cell-dependent anti-tumor immunity that can result in durable complete responses. Recent advances in protocols that utilize DC electroporated with autologous tumor RNA (AGS-003) have led to sustained immune responses with improved patient survival. Circulating monocytes are the most common source material that is matured ex vivo into dendritic cells. This heterogeneous population consists of ~90% classical (CD14+ CD16−), ~5% intermediate (CD14+ CD16+), and ~5% non-classical (CD14dimCD16+) monocytes in healthy donors. The behavior of these distinct subsets has only recently been defined by a few publications that observed increased patrolling behavior of non-classical monocytes. Very little information is available regarding the fate of subsets upon differentiation into dendritic cells.

The findings described herein demonstrate that dendritic cells derived from non-classical monocytes have increased expression of molecules important for T cell activation and lead to improved efficacy of vaccines by promoting T cell-dependent anti-tumor responses. To increase costimulatory molecule expression on monocyte-derived dendritic cells, provided herein are compositions and methods for converting the predominant circulating classical monocytes to a non-classical monocyte phenotype through cytokine stimulation via, for example, macrophage colony-stimulating factor. Once cultured into dendritic cells, these non-classical monocyte derived cells have increased costimulatory molecule expression, which leads to improved immune and clinical responses in cancer patients receiving dendritic cell vaccination. A number of commercial dendritic cell vaccine approaches are currently in Phase 1, 2 and 3 assessment for a variety of cancers. The most prominent dendritic cell-vaccine product is the FDA-approved product Sipuleucel-T for metastatic prostate cancer. The compositions and methods described herein are useful for all dendritic cell vaccines that originate from monocytes.

Dendritic cell (DC) vaccination is a patient-specific therapy that can induce durable cancer-specific immune responses capable of reducing tumor burden in up to 50% of stage IV cancer patients with 18% resulting in complete responses. Circulating monocytes are the conventional starting material used in DC protocols. Several subsets of monocytes have been described (classical, intermediate, and non-classical). However, the precise differentiation patterns of these subsets resulting in DC that can activate T cells are unknown. As demonstrated herein, dendritic cells derived from the non-classical monocyte subset represent the most potent antigen presenting cells for use in dendritic cell vaccination. The studies described herein investigate monocyte subsets from renal cell carcinoma (RCC) patients who were treated with DC vaccines and from healthy donors to determine whether enrichment of discrete subsets in culture can improve DC activation of T cells. These studies are based on the finding that DCs derived from non-classical monocytes have improved costimulatory molecule expression and that pretreatment, circulating non-classical monocytes are more abundant by more than two-fold in complete responders to DC vaccination.

The translational studies described herein compare DCs derived from nonclassical and classical monocytes for their ability to activate T cells. The rationale for these studies is based on the discovery described herein that upon maturation into DCs, non-classical and intermediate monocytes express higher levels of costimulatory molecules that are vital components to T cell activation. Accordingly, DCs derived from the non-classical monocyte subset represent the most potent antigen presenting cells for use in dendritic cell vaccination. As also described herein, cytokine stimulation of peripheral blood monocytes, for example using macrophage colony-stimulating factor (M-CSF), can enrich for the non-classical subset, resulting in DCs that are superior activators of T cells, which has broad impact on DC vaccine protocols and consequent patient survival. In addition, these studies have direct implications for DC vaccines that are either commercially available (Sipuleucel-T for prostate cancer) or in Phase III testing, such as AGS-003 for advanced or localized RCC (IND #16047) and DEC-205-NY-ESO-1 (IND #14939) for NY-ESO-1 positive solid cancers. In addition, pre-treatment of peripheral blood from RCC cancer patients is performed to determine if the percentage and gene expression signature of monocyte subsets is different amongst patients who respond to DC vaccination, thereby providing new biomarkers to predict patient responses to immunotherapy.

The studies described herein use aliquots from the same blood specimens from Stage IV RCC patients that are cultured into DCs and later used in vaccination. Importantly, these studies cannot be performed in murine models due to differences in monocyte subset phenotypes.

As described herein, dendritic cells derived from the minor non-classical and intermediate monocyte populations express the highest levels of costimulatory molecules. Cancer patients have been treated with monocyte-derived DC for more than 15 years and a small population of Stage IV patients demonstrate complete responses. However, surprisingly little is known with regards to which monocyte subsets are the best antigen presenting cells once they are cultured into DC. To address this gap, monocyte subsets were isolated based on the expression of CD14 (co-receptor for toll-like receptor 4) and CD16 (Fcγ receptor III) from peripheral blood of healthy donors using flow-sorting techniques (90% pure for desired cells). Subsets were then fluorescently labelled and cultured with GM-CSF and IL-4 and matured on day 7 with the cytokines 1L-6, IL-113, and TNF-α and Prostaglandin E2. Mature DC were harvested, stained for costimulatory molecules (CD80, CD86, HLA-DR) and analyzed by flow cytometry. DC derived from all monocyte populations expressed CD80 (FIG. 2A, 65% positive), CD86 (FIG. 2B), and HLA-DR at levels that are acceptable for injection into patients as mature DC. HLA-DR' DC that were derived from intermediate and non-classical monocytes had greater percentage of cells positive for CD80 (FIG. 1) and CD86. These costimulatory molecules have each been shown to impact T cell activation, indicating that DC derived from non-classical and intermediate monocytes represent the most potent antigen presenting cells. Importantly, clinical trials have also demonstrated that CD80 and CD86 expression on DC can be indicators for clinical response.

Figure 3:
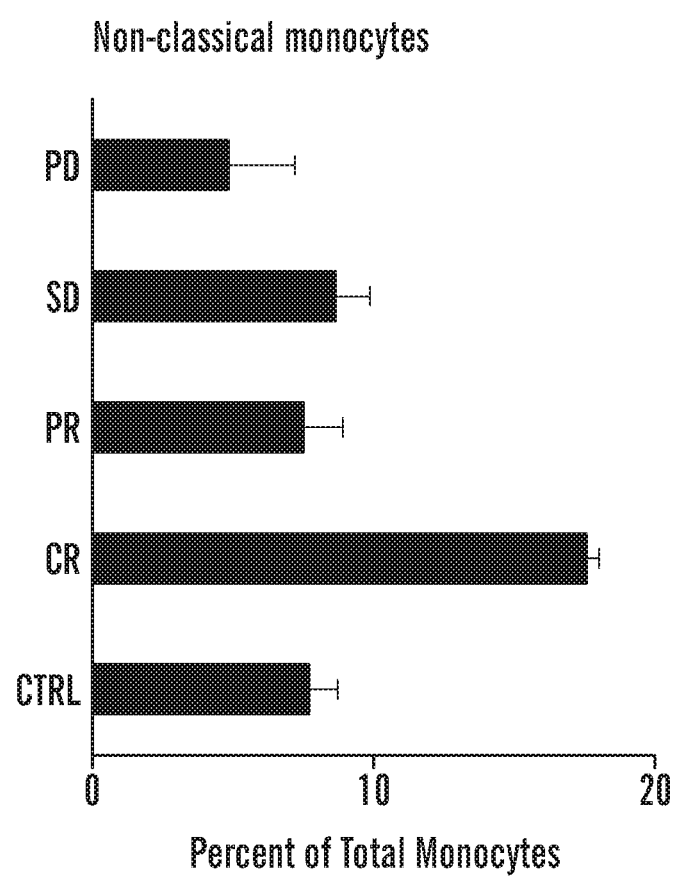
FIG. 3 demonstrates that non-classical monocytes are increased in pretreatment samples of complete responders to dendritic cell vaccination. The percentage of circulating non-classical monocytes was evaluated by flow cytometry in pretreatment samples from 13 Stage IV RCC patients (CR, complete response; PR, partial response; SD, stable disease; PD, progression of disease) and 4 healthy donors (CTRL). *P<0.05 versus all other groups.
Figure 4:
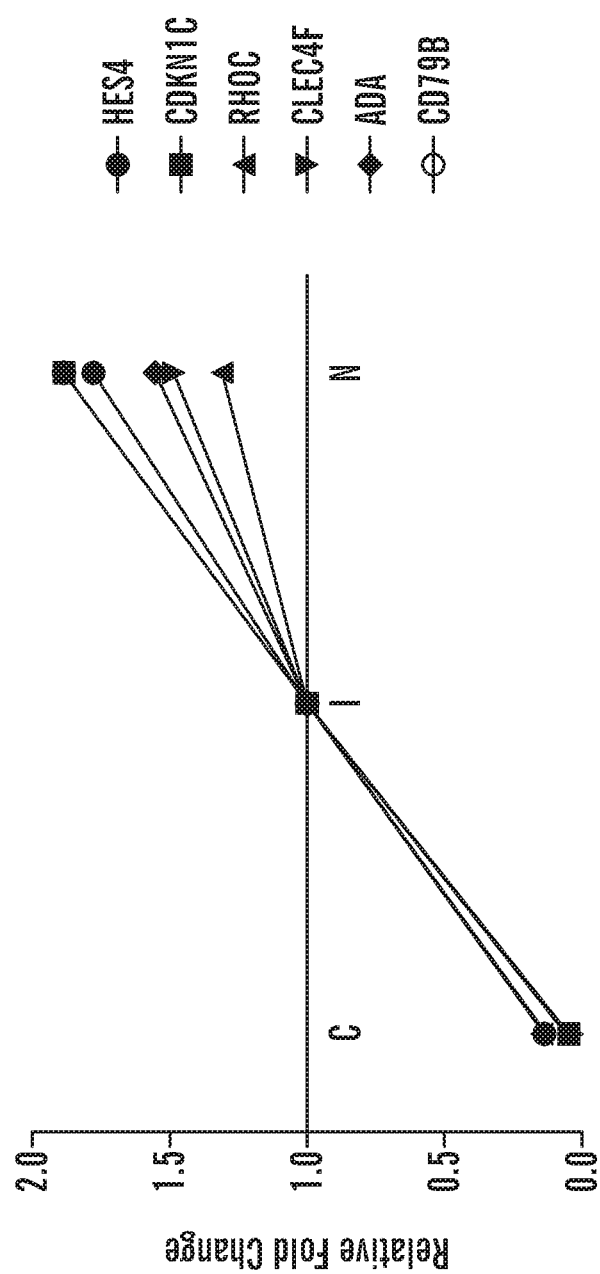
FIG. 4 demonstrates that genes highly expressed by non-classical monocytes are consistent with published findings (Wong K. L. et al (2011) Blood 118: 5). Gene expression on RNA isolated from monocyte subsets (Classical (C), Intermediate (I), and non-classical (N)) was evaluated by Illumina Human HT12v4 microarray assay. Gene expression shown to be elevated in non-classical monocytes was normalized to intermediate monocytes, demonstrating that intermediate monocytes had expression in between classical and non-classical subsets.

As described herein, circulating non-classical and intermediate monocytes are increased more than two-fold in complete responders to dendritic cell vaccination. The status of circulating non-classical and intermediate subsets of monocytes in cancer patients has not been well characterized. To evaluate if monocyte subset composition was altered in RCC patients, flow cytometry of pre-treatment peripheral blood monocytes from 13 Stage IV RCC patients who received intranodal autologous tumor lysate DC vaccinations and 4 healthy controls was performed. Monocyte subsets were evaluated and sorted based on HLA-DR, CD14, and CD16 expression with a BD FACSARIA™ (BD Biosciences) flow cytometer. It was found that Stage IV RCC complete responders (CR) to DC vaccination exhibited a unique monocyte subset signature (FIG. 3). Specifically, CR specimens had twice as many non-classical monocytes (16.3%±2.6, mean±SD) than the blood of partial responders (6.8%±2.8, P<0.01), patients with progressive disease (4.5%±3.9, P<0.05), or healthy donors (7.2%±2.6 P<0.005). Peripheral blood from complete responders also contained more intermediate monocytes and fewer classical monocytes. Importantly, total RNA was also isolated from these samples for microarray analysis, which confirmed that the analyzed subsets were in fact classical, intermediate, and non-classical (FIG. 4).

Collectively, these studies provide the first evidence that the percentage of circulating non-classical monocytes prior to treatment correlates with clinical response to DC vaccination. Evidence that DC derived from non-classical monocytes have higher costimulatory molecule expression indicate that enrichment of these $CD14^{dim}$, $CD16^+$ cells prior to DC maturation can enhance the DC vaccine product and improve clinical responses to DC vaccination. Current DC vaccine protocols positively select $CD14^+$ monocytes, thus removing non-classical monocytes ($CD14^{dim}$), thereby limiting anti-tumor immune responses. Accordingly, the findings described herein impact patient responses to DC vaccination by improving patient selection, as well as enhancing the injected DC products.

As described herein, DCs derived from non-classical monocytes are superior activators of T cell-mediated anti-tumor immunity compared to the predominant classical subset of monocytes and cytokine stimulation of heterogeneous monocyte populations can enrich for the non-classical subset.

Figure 2A:
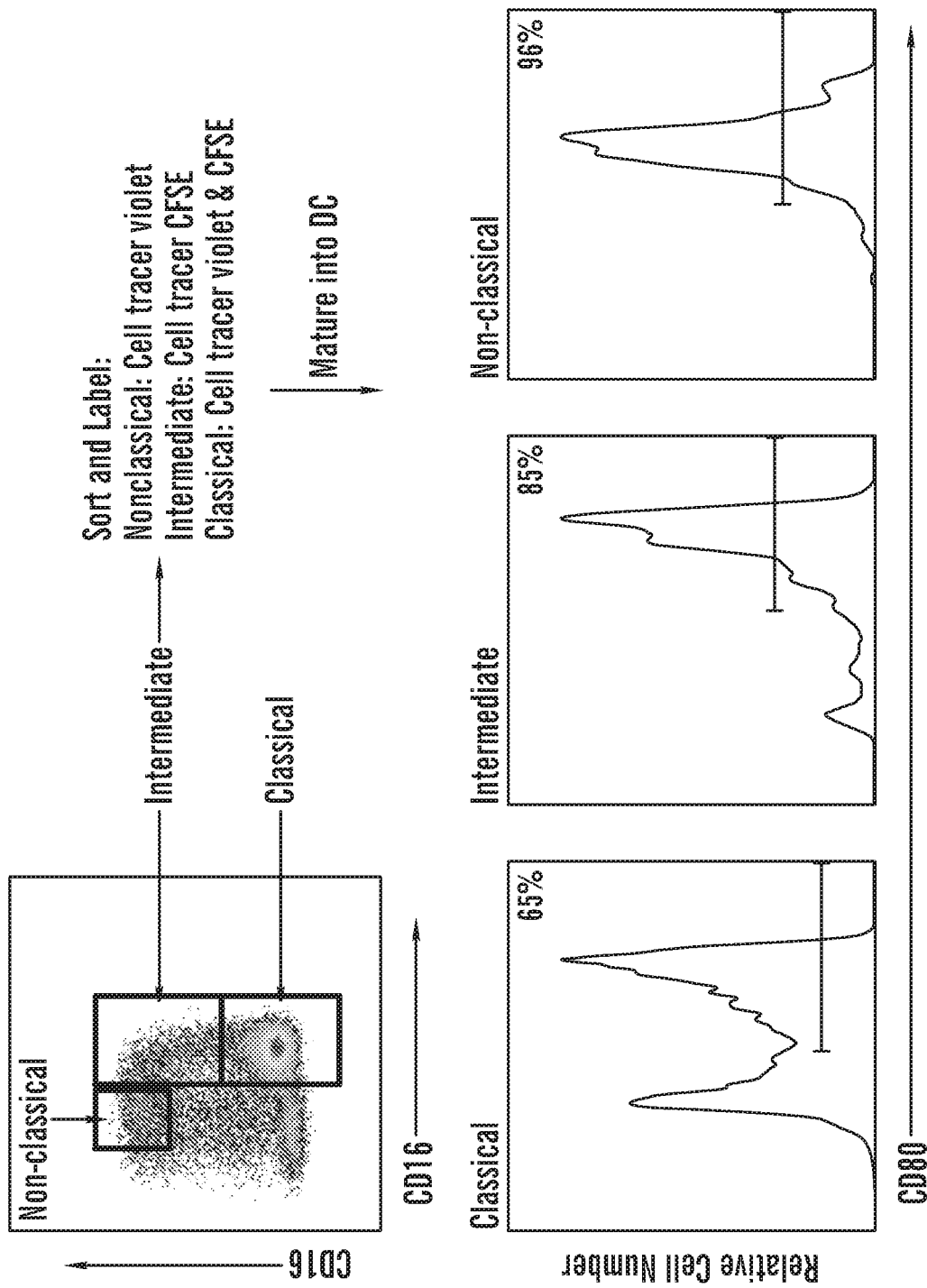
FIGS. 2A-2B demonstrate that dendritic cells derived from intermediate and non-classical monocytes have an increased percentage of CD80$^+$ and CD86$^-$ cells. Classical (CD16$^-$ CD14$^+$), intermediate (CD16$^+$, CD14$^+$), and non-classical (CD16$^+$CD14$^{dim}$) monocytes were isolated by flow sorting and labelled with fluorescent dyes. Monocytes were grown under conventional culture techniques. Cells were stained for CD80 (FIG. 2A), CD86 (FIG. 2B), and HLA-DR. Data are representative of n=3 independent experiments. Number above bracketed line indicates percent positive based on isotype control.
Figure 2B:
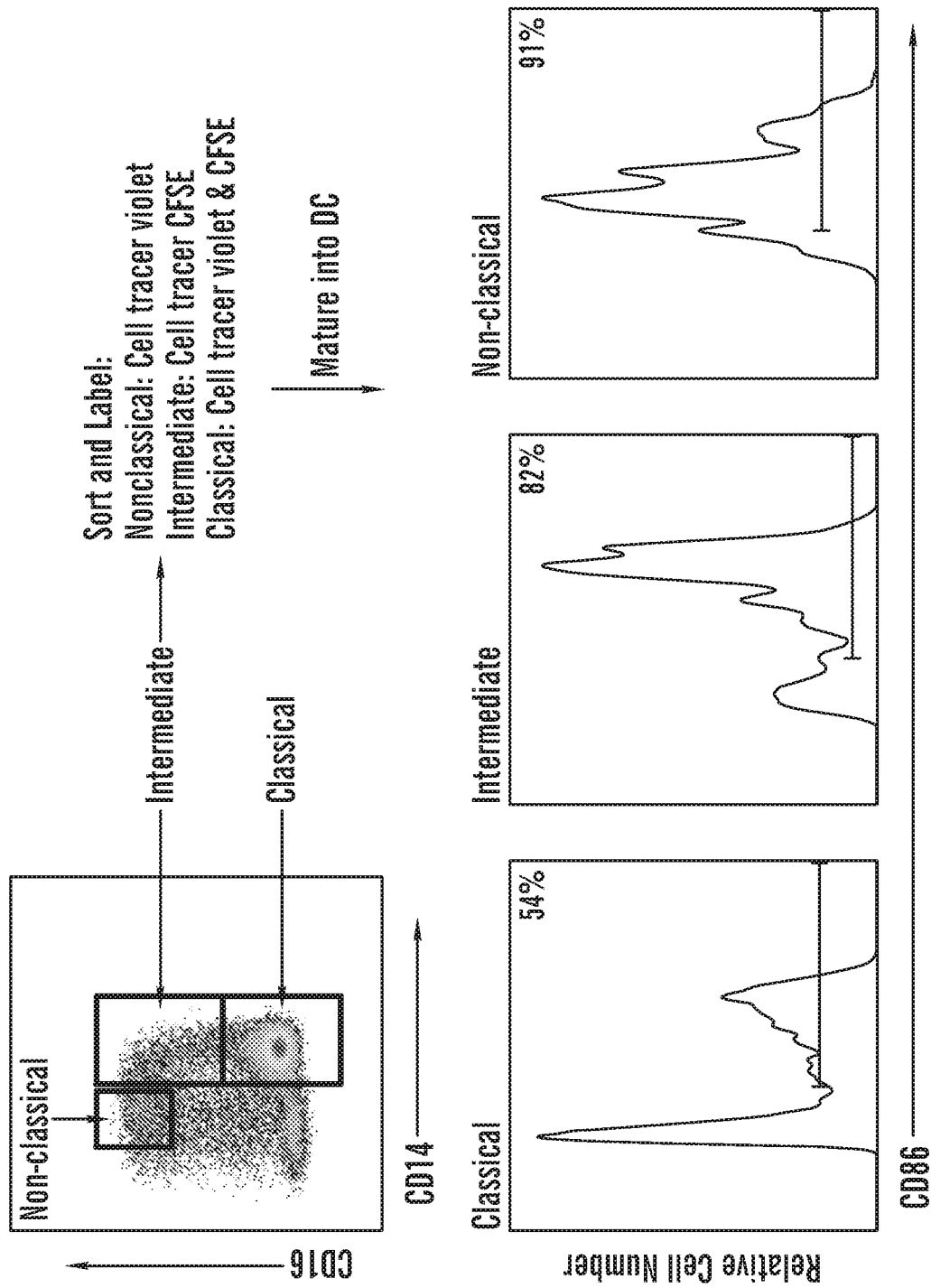

DC vaccine protocols that utilize heterogeneous peripheral blood monocytes as starting material have been used for treatment of cancer patients for more than fifteen years. Areas of investigation include whether monocytes can transition from one subset to another, and the fate of discrete monocyte subsets once they are differentiated into DC via cytokine stimulation. As shown herein, cytokine stimulation of heterogeneous monocyte populations can enrich the minor non-classical monocyte subset and improve dendritic cell-mediated activation of T cells. We found that DC derived from the non-classical and intermediate monocytes have increased numbers of cells positive for CD80 (FIG. 2A), and CD86 (FIG. 2B). DC expression of these costimulatory molecules has been shown to impact T cell activation. Since non-classical ($CD14^{dim}$, $CD16^+$) and intermediate ($CD14^+$, $CD16^+$) monocytes together make up only about 10% of circulating monocytes in healthy donors and cancer patients (FIG. 3), increasing these populations will improve T cell activation by the resultant DC product.

The experiments described herein determine if cytokine stimulation of classical monocytes can induce transition to intermediate followed by non-classical phenotype. Circulating monocyte subsets are isolated from healthy donors and stimulated with cytokines and later examined for CD14 and CD16 expression. Monocytes have been isolated from healthy donors and RCC patients based on CD14 and CD16 expression (FIGS. 2A-2B, 3). Microarray analysis of these sorted monocyte subpopulations found that six of the genes that are most different between classical and non-classical monocytes were also different in our sorted populations, confirming successful isolation of the separate populations (FIG. 4). Notably, intermediate monocytes expressed genes at levels between nonclassical and classical, indicating that they may indeed represent a transitional cell population.

The experiments described herein also evaluate the plasticity of monocyte subsets. While cytokine stimulation with M-CSF, TGF-β1, and MCP-1 have all been shown to increase CD16 expression on monocytes in vitro, the ability of these cytokines to drive classical monocytes ($CD16^-$, $CD14^+$) to a non-classical phenotype ($CD16^+$, $CD14^{dim}$) has not been previously reported. A recent phase 1 trial of rheumatoid arthritis patients has shown that blockade of M-CSF binding to M-CSF receptor can reduce circulating non-classical and intermediate monocytes to below the limits of detection. Following cessation of treatment, intermediate monocytes appear first in circulation followed days later by non-classical monocytes indicating that intermediate monocytes serve as a transitional cell before fully differentiating into non-classical monocytes. Different reports on whether M-CSF promotes CD16 expression in vitro have clouded interpretation of in vivo human data demonstrating that M-CSF treatment induces CD16+ populations. As described herein, circulating monocyte subsets are isolated from healthy donors and cultured with M-CSF to determine whether classical monocytes transition to intermediate and then non-classical monocytes (FIG. 1). Circulating monocyte subsets are also isolated from healthy donors and cultured with other cytokines that are reported to induce CD16, such as TGF-β1 and MCP-1.

The experiments described herein also evaluate monocyte subset influences on DC behavior. Increased expression of costimulatory molecules by DC derived from non-classical monocytes can improve efficacy of vaccines by promoting T cell responses. To directly assess the ability of DC derived from each subset to activate T cells, expansion of antigen specific T cells upon culture with DC that have been pulsed with antigen is monitored. Circulating monocyte subsets of HLA-A2 healthy donors are isolated via flow cytometry based on CD14 and CD16 expression (FIGS. 2A-2B). Monocyte subsets are cultured in media for 7 days with GM-CSF and IL-4 followed by maturation with IL-6, IL-1β, TNF-α, and prostaglandin $E_2$ (a maturation cocktail) on day 7. The MART-1 antigen is utilized as a model system to assess T cell proliferation due to the relatively high percentage of T cells specific for MART-1 in HLA-A2* healthy donors. Upon maturation, DCs are pulsed with the immunodominant MART-1 peptide LAGIGILTV (SEQ ID NO: 1), and cultured with $CD8^+$ T cells from $HLA-A2^+$ donors purified via CD8+ T cell Isolation kit (Miltenyi Biotec). MART-1-specific $CD8^+$ T cells are identified by flow cytometry with a MART-1 pentamer and anti-CD8 antibody. DC derived from monocyte subsets are further characterized by evaluating cytokine secretion by Multiplex assays. Differentiating non-classical monocytes derived via cytokine stimulation can also be evaluated for DC derivation using these assays.

The experiments described herein show that the composition and gene expression signature of pre-treatment, circulating monocyte subsets predicts outcome of renal cell carcinoma patients to DC vaccination. Monocyte subsets have been studied in numerous inflammatory conditions, but they have not been well characterized in cancer patients. Only a handful of studies have evaluated the $CD16^+$ monocytes in cancer patients, and these did not distinguish intermediate and nonclassical subsets. There are no published findings documenting the percentage or function of circulating monocyte subsets (classical, intermediate, and non-classical) in cancer patients treated with immunotherapy. Based on the data described herein from a completed DC clinical trial that complete responders had increased non-classical monocytes prior to treatment (FIG. 3), it was evaluated whether the percentage and gene profile signature of circulating monocyte subsets can predict patient responses to immunotherapy.

Figure 5:
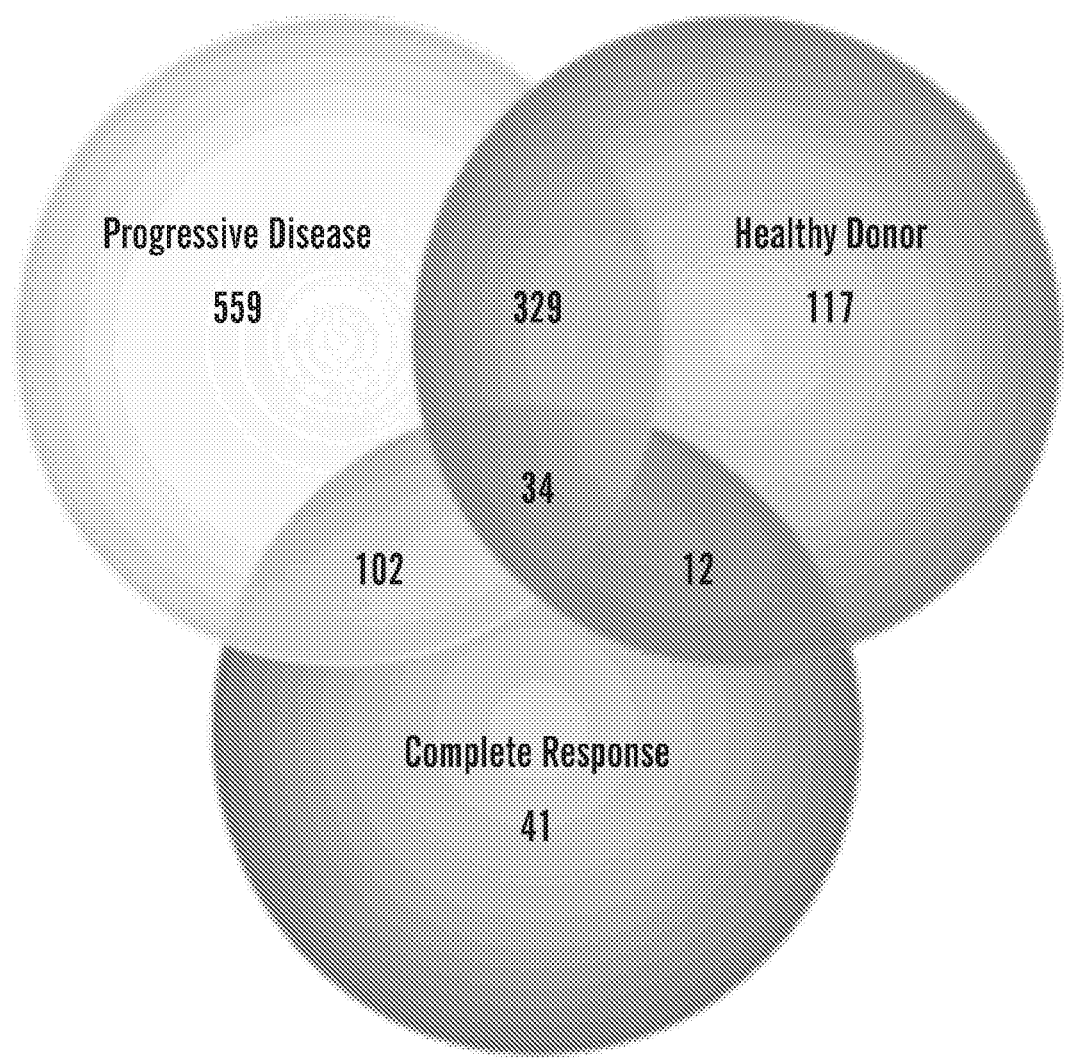
FIG. 5 demonstrates that microarray analysis of non-classical monocyte RNA reveals gene expression changes between complete responders and non-responders responding to DC vaccination. Venn diagram depicts the number of genes with >1.5 fold changes in healthy donors, complete responders or patients with progressive disease.

An analysis of peripheral blood samples from a trial of stage IV RCC patients treated with autologous tumor lysate DC vaccination was performed. It was found that complete responders had increased non-classical monocytes (FIG. 3). Similar to the findings described herein of patients who had no or partial responses, others have found no difference in the frequency of non-classical and classical monocyte populations amongst RCC patients compared to healthy controls. A microarray analysis of RNA samples from all three monocyte subsets was performed from one healthy control, one RCC patient who had progressive disease following DC vaccine, and two RCC patients with complete responses. The analyses described herein demonstrate that RCC patients who did not respond to DC vaccine had a large number of differentially expressed genes (559) compared to complete responders or healthy controls (FIG. 5). It was also determined that a number of genes were different in complete responders compared to non-responders and healthy controls.

Data shown herein demonstrate that dendritic cells (DC) derived from the non-classical and intermediate monocytes are superior activators of T cells compared to DC from the predominant classical monocyte subset. These findings showed that DC derived from intermediate and non-classical monocytes had higher levels of costimulatory molecules that are necessary for T cell activation. As shown in FIGS. 2A-2B, dendritic cells (DC) derived from intermediate (CD14+, CD16+) or non-classical (CD14low, CD16+) monocytes have higher levels of costimulatory molecules than DC from classical (CD14+, CD16low) monocytes. Each monocyte subset was sorted by flow cytometry and then cultured into DC. Following DC maturation, the surface expression of CD80, CD83, and CD86 were evaluated on HLA-DR+ DC.

Figure 6:
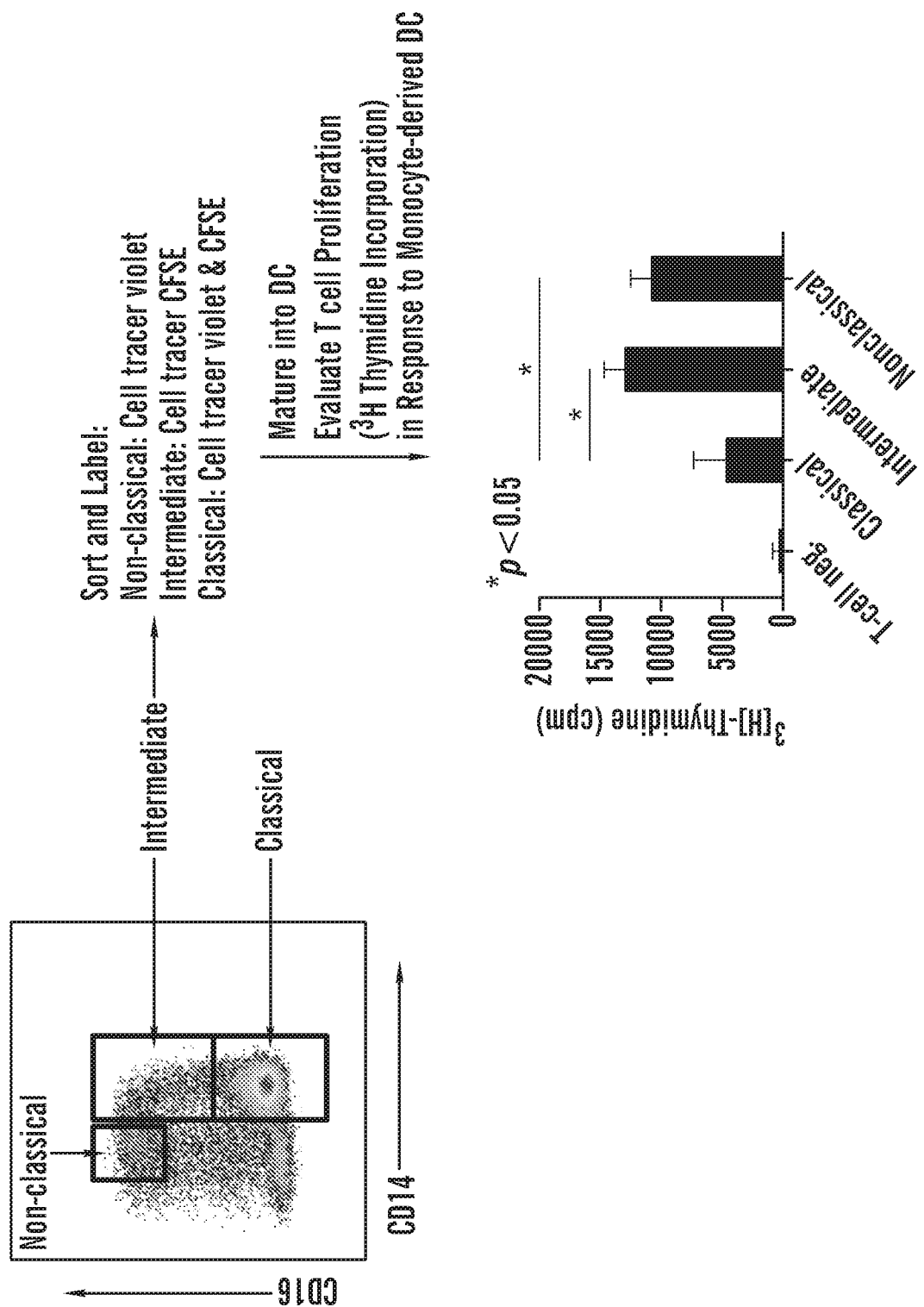
FIG. 6 demonstrates that dendritic cells (DC) derived from intermediate (CD14$^+$, CD16$^+$) or non-classical (CD14$^{low}$, CD16$^-$) monocytes induce increased proliferation of allogeneic T cells relative to DC from classical (CD14$^+$, CD16$^{low}$) monocytes. Monocytes were isolated from peripheral blood and cultured into DC. The data show $^3$[H]thymidine incorporation by human allogeneic T cells (CD4 and CD8) cultured for 5 d with DCs derived from classical, intermediate, or non-classical monocytes or the mitogen PHA as a positive control proliferation. Data are representative of one of two independent experiments (mean±s.e.m.).

Further experiments have demonstrated that DCs from intermediate and non-classical monocytes are superior T cell activators compared to DCs derived from classical monocytes. FIG. 6 demonstrates that dendritic cells (DC) derived from intermediate (CD14$^+$, CD16$^+$) or non-classical (CD14$^{low}$, CD16$^+$) monocytes induce increased proliferation of allogeneic T cells relative to DC from classical (CD14$^+$, CD16$^{low}$) monocytes. Monocytes were isolated from peripheral blood and cultured into DC.

The experiments described herein confirm the findings that the gene expression signature and composition of monocyte subsets is different for responders prior to DC vaccination. This is achieved by characterizing circulating subsets in RCC patients with localized disease enrolled in a worldwide first clinical trial that utilizes DC electroporated with tumor RNA as a neoadjuvant therapy (AGS-003 DC, IND #16047). Monocyte subsets are monitored from pre-treatment peripheral blood samples using flow cytometric detection of CD14 and CD16 (FIGS. 2, 3). In order to compare gene expression between healthy controls, non-responders, and responders to DC therapy, monocyte subsets are flow sorted and RNA harvested from each subset for microarray analysis. The findings on monocyte subsets with costimulatory molecule expression are compared on an aliquot of the same DC material used for vaccination. To determine if gene products identified in these screens that are known to be expressed on the surface of cells represent biomarkers for patient response to treatment, protein expression is evaluated by flow cytometry. Microarray results are confirmed using real-time PCR and perform bioinformatic analysis of the data to identify gene pathways that are altered in circulating monocyte populations of non-responders and responders. These findings have broad implications in cancer treatment.

During the analyses of the completed DC clinical trial for metastatic RCC patients, RNA was isolated from 5 partial responders, 3 stable disease and 3 patients with progressive disease. While none of these patients experienced complete response, 3-year survival was 70%, which is a marked improvement above the 29% historical comparison. Additional gene pathways are examined by performing microarray analysis of monocyte subsets from partial responders and patients with stable disease and compared with subsets from patients whose disease progressed following DC vaccination to determine genes relevant to patient survival.

To evaluate immune responses to DC therapy, circulating and intratumoral CD28$^+$, CCR7+, CD45RA– memory CD8 T cells are quantified, which, when elevated following DC vaccination, have been shown to correlate with patient responses and survival. Flow cytometry protocols have been developed to detect these T cells along with effector and naive CD8 and CD4 T cells in peripheral blood and RCC tumors. Endpoints of flow cytometry data evaluating costimulatory molecule expression are considered suitably continuous and are analyzed using standard analysis-of-variance (ANOVA) methods.

Identification of mechanisms responsible for transition of monocytes from one subset to another can have an immediate impact on immunotherapy protocols. In the event that, due to the size and design of the AGS-003 trial (tumors are surgically removed), patients do not have complete responses, and responses to the vaccine are difficult to measure, immune responders to DC vaccine can be evaluated using the other methods described herein. Monocytes from pre-treatment samples of stage IV RCC patients who received AGS-003 DC and had long-term responses with minimal residual disease are also analyzed.

We claim:

1. A method to increase efficacy of an immunotherapy comprising:
   a) contacting a sample comprising monocytes or monocyte progenitors with one or more cytokines comprising MCP-1, wherein the one or more cytokines promote the transition of monocytes or monocyte progenitors in said sample to a non-classical and/or intermediate phenotype and incubating said monocytes under conditions that permit said transition, thereby enriching the monocytes for a population of non-classical and/or intermediate monocytes derived from the sample of monocytes, wherein the population of non-classical monocytes is $CD16^+$ and $CD14^{dim}/CD14^-$ and the population of intermediate monocytes is $CD16^+$ and $CD14^+$;

b) isolating non-classical and/or intermediate monocytes from the enriched population; and then c) culturing the isolated non-classical and/or intermediate monocytes in a dendritic cell maturation cocktail, under conditions that permit dendritic cell differentiation to generate dendritic cells with enhanced efficacy in an immunotherapy.

2. The method of claim 1, wherein dendritic cells derived from said non-classical and/or intermediate monocytes have increased expression of one or more co-stimulatory molecules relative to a population derived from $CD14^+CD16^-$ monocytes.

3. The method of claim 2, wherein the one or more co-stimulatory molecules is selected from CD80, CD83, CD86, and MHC Class II.

4. The method of claim 1, further comprising enrichment by cell sorting.

5. The method of claim 1, wherein the sample of monocytes is from a cancer patient.

6. The method of claim 1, wherein said immunotherapy comprises a dendritic cell vaccine.

7. The method of claim 1, wherein the one or more cytokines further comprise M-CSF and/or TGF-β.

8. The method of claim 1, wherein step (a) enriches the monocytes for non-classical and/or intermediate monocytes such that non-classical and/or intermediate monocytes comprise at least 15% of the population.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Ala Gly Ile Gly Ile Leu Thr Val
1               5
```